(12) United States Patent (10) Patent No.: US 8,452,421 B2
Thenuwara et al. (45) Date of Patent: May 28, 2013

(54) LEAD INSERTION TOOLS

(75) Inventors: Chuladatta Thenuwara, Castaic, CA (US); Thomas H. R. Lenarz, Hannover (DE); Mark Downing, Valencia, CA (US)

(73) Assignee: Advanced Bionics, LLC, Valencia, CA (US)

( * ) Notice: Subject to any disclaimer, the term of this patent is extended or adjusted under 35 U.S.C. 154(b) by 386 days.

(21) Appl. No.: 12/832,745

(22) Filed: Jul. 8, 2010

(65) Prior Publication Data

US 2011/0009877 A1 Jan. 13, 2011

Related U.S. Application Data

(60) Provisional application No. 61/223,774, filed on Jul. 8, 2009.

(51) Int. Cl.
*A61N 1/372* (2006.01)
*A61N 1/05* (2006.01)

(52) U.S. Cl.
CPC .................................. *A61N 1/0541* (2013.01)
USPC .............. 607/137; 607/116; 607/57; 600/379

(58) Field of Classification Search
USPC ............... 607/55–57, 137, 115, 116; 600/379
See application file for complete search history.

(56) References Cited

U.S. PATENT DOCUMENTS

| | | | |
|---|---|---|---|
| 3,530,860 A | 9/1970 | Majoros | |
| 3,973,560 A | 8/1976 | Emmett | |
| 4,180,080 A | 12/1979 | Murphy | |
| 4,280,510 A | 7/1981 | O'Neill | |
| 4,488,561 A | 12/1984 | Doring | |
| 4,532,930 A | 8/1985 | Crosby et al. | |
| 4,646,755 A | 3/1987 | Kane | |
| 4,665,918 A | 5/1987 | Garza et al. | |
| 4,787,884 A | 11/1988 | Goldberg | |
| 4,819,647 A | 4/1989 | Byers et al. | |
| 4,865,037 A | 9/1989 | Chin et al. | |

(Continued)

FOREIGN PATENT DOCUMENTS

| | | |
|---|---|---|
| EP | 0109304 | 5/1984 |
| EP | 0328597 | 8/1989 |

(Continued)

OTHER PUBLICATIONS

International Search Report and Written Opinion received in International Application No. PCT/US2011/041576, dated Sep. 19, 2011.

(Continued)

*Primary Examiner* — Carl H Layno
*Assistant Examiner* — Eugene Wu
(74) *Attorney, Agent, or Firm* — ALG Intellectual Property, LLC

(57) ABSTRACT

An exemplary insertion tool configured to facilitate insertion of a lead into a bodily orifice includes a handle assembly configured to facilitate handling of the insertion tool, an insertion assembly coupled to the handle assembly and comprising a rigid holding tube configured to removably couple to a portion of the lead, and a release assembly disposed at least partially within the handle assembly and comprising a release button. The release assembly is configured to release the lead from the holding tube in response to user actuation of the release button. Corresponding insertion tools, systems, and methods are also described.

20 Claims, 20 Drawing Sheets

U.S. PATENT DOCUMENTS

| | | | |
|---|---|---|---|
| 4,898,183 A | 2/1990 | Kuzma | |
| 4,994,069 A | 2/1991 | Ritchart et al. | |
| 5,046,497 A | 9/1991 | Millar | |
| 5,110,529 A | 5/1992 | Arima | |
| 5,159,861 A | 11/1992 | Anderson | |
| 5,312,415 A | 5/1994 | Palermo | |
| 5,314,464 A | 5/1994 | KenKnight et al. | |
| 5,443,493 A * | 8/1995 | Byers et al. | 607/137 |
| 5,545,200 A | 8/1996 | West et al. | |
| 5,545,219 A | 8/1996 | Kuzma | |
| 5,558,673 A | 9/1996 | Edwards et al. | |
| 5,645,585 A | 7/1997 | Kuzma | |
| 5,667,514 A | 9/1997 | Heller | |
| 5,810,852 A | 9/1998 | Greenberg et al. | |
| 5,814,062 A | 9/1998 | Sepetka et al. | |
| 5,902,331 A | 5/1999 | Bonner et al. | |
| 5,906,619 A | 5/1999 | Olson et al. | |
| 5,999,859 A | 12/1999 | Jolly | |
| 6,070,105 A | 5/2000 | Kuzma | |
| 6,071,282 A | 6/2000 | Fleischman | |
| 6,078,841 A | 6/2000 | Kuzma | |
| 6,093,197 A | 7/2000 | Bakula et al. | |
| 6,119,044 A | 9/2000 | Kuzma | |
| 6,125,302 A | 9/2000 | Kuzma | |
| 6,129,753 A | 10/2000 | Kuzma | |
| 6,149,657 A | 11/2000 | Kuzma | |
| 6,163,729 A | 12/2000 | Kuzma | |
| 6,195,586 B1 | 2/2001 | Kuzma | |
| 6,208,882 B1 | 3/2001 | Lenarz et al. | |
| 6,219,580 B1 | 4/2001 | Faltys et al. | |
| 6,272,382 B1 | 8/2001 | Faltys et al. | |
| 6,293,945 B1 | 9/2001 | Parins et al. | |
| 6,304,785 B1 | 10/2001 | McCreery et al. | |
| 6,308,101 B1 | 10/2001 | Faltys et al. | |
| 6,321,125 B1 | 11/2001 | Kuzma | |
| 6,421,569 B1 | 7/2002 | Treaba et al. | |
| 6,500,130 B2 | 12/2002 | Kinsella et al. | |
| 6,547,762 B1 | 4/2003 | Botich et al. | |
| 6,582,441 B1 | 6/2003 | He et al. | |
| 6,604,283 B1 | 8/2003 | Kuzma | |
| 6,746,412 B1 | 6/2004 | Hill et al. | |
| 6,858,034 B1 | 2/2005 | Hijlkema et al. | |
| 6,866,669 B2 | 3/2005 | Buzzard | |
| 6,936,065 B2 | 8/2005 | Khan et al. | |
| 6,939,352 B2 | 9/2005 | Buzzard | |
| 6,968,238 B1 * | 11/2005 | Kuzma | 607/137 |
| 7,050,858 B1 * | 5/2006 | Kuzma et al. | 607/137 |
| 7,063,708 B2 | 6/2006 | Gibson et al. | |
| 7,269,461 B2 | 9/2007 | Dadd et al. | |
| 7,349,744 B2 | 3/2008 | Dadd et al. | |
| 7,544,197 B2 | 6/2009 | Kelsch et al. | |
| 7,591,268 B2 | 9/2009 | Lowe et al. | |
| 7,792,586 B2 | 9/2010 | Dadd et al. | |
| 7,966,077 B2 | 6/2011 | Risi | |
| 2002/0045927 A1 | 4/2002 | Moore et al. | |
| 2002/0143302 A1 | 10/2002 | Hinchliffe et al. | |
| 2002/0147484 A1 | 10/2002 | Dahl | |
| 2003/0045921 A1 | 3/2003 | Dadd et al. | |
| 2003/0093139 A1 | 5/2003 | Gibson et al. | |
| 2003/0171758 A1 * | 9/2003 | Gibson et al. | 606/129 |
| 2004/0127968 A1 | 7/2004 | Kuzma et al. | |
| 2004/0193203 A1 | 9/2004 | Pak et al. | |
| 2004/0220651 A1 | 11/2004 | Kuzma et al. | |
| 2004/0243177 A1 | 12/2004 | Svehla et al. | |
| 2004/0260371 A1 | 12/2004 | Greenland et al. | |
| 2005/0004644 A1 | 1/2005 | Kelsch et al. | |
| 2005/0075606 A1 | 4/2005 | Botich et al. | |
| 2005/0251237 A1 | 11/2005 | Kuzma et al. | |
| 2006/0058861 A1 | 3/2006 | Gibson et al. | |
| 2006/0155353 A1 | 7/2006 | Heil, Jr. | |
| 2006/0241723 A1 * | 10/2006 | Dadd et al. | 607/57 |
| 2007/0043419 A1 | 2/2007 | Nikolchev et al. | |
| 2007/0111175 A1 | 5/2007 | Raven et al. | |
| 2007/0213812 A1 | 9/2007 | Webler et al. | |
| 2007/0233214 A1 | 10/2007 | Chitre et al. | |
| 2008/0004684 A1 | 1/2008 | Dadd et al. | |
| 2008/0082141 A1 | 4/2008 | Risi | |
| 2008/0109011 A1 | 5/2008 | Thenuwara et al. | |
| 2008/0195146 A1 | 8/2008 | Wardle | |
| 2008/0269740 A1 | 10/2008 | Bonde et al. | |
| 2008/0269763 A1 * | 10/2008 | Bonde et al. | 606/99 |
| 2009/0119920 A1 | 5/2009 | Peschke et al. | |
| 2011/0301681 A1 | 12/2011 | Risi | |

FOREIGN PATENT DOCUMENTS

| | | |
|---|---|---|
| EP | 1233810 | 8/2002 |
| EP | 1341578 | 9/2003 |
| EP | 1370205 | 12/2003 |
| EP | 1476104 | 11/2004 |
| EP | 2039323 | 3/2009 |
| WO | WO-80/02231 | 10/1980 |
| WO | WO-8900870 | 2/1989 |
| WO | WO-9324058 | 12/1993 |
| WO | WO-95/11710 | 5/1995 |
| WO | WO-9720530 | 6/1997 |
| WO | WO-00/64529 | 11/2000 |
| WO | WO-00/71063 | 11/2000 |
| WO | WO-01/68177 | 9/2001 |
| WO | WO-02/30507 | 4/2002 |
| WO | WO-0230507 | 4/2002 |
| WO | WO-0232498 | 4/2002 |
| WO | WO-02074211 | 9/2002 |
| WO | WO-03/070133 | 8/2003 |
| WO | WO-03070133 | 8/2003 |
| WO | WO-2004/014472 | 2/2004 |
| WO | WO-2004012809 | 2/2004 |
| WO | WO-2005/110529 | 11/2005 |
| WO | WO-2010/045228 A3 | 4/2010 |
| WO | WO-2010/133704 A2 | 11/2010 |
| WO | WO-2011/005993 A1 | 1/2011 |

OTHER PUBLICATIONS

Non-Final Office Action received in U.S. Appl. No. 12/425,868, dated Nov. 25, 2011.

International Search Report and Written Opinion received in International Application No. PCT/US2011/041577, dated Nov. 30, 2011.

Non-Final Office Action received in U.S. Appl. No. 12/824,120, dated Jun. 8, 2012.

Non-Final Office Action received in U.S. Appl. No. 12/824,119, dated Jun. 8, 2012.

Final Office Action received in U.S. Appl. No. 12/425,868, dated Jul. 6, 2012.

International Search Report and Written Opinion received in International Application No. PCT/US2007/083428 dated May 20, 2008.

* cited by examiner

LEAD INSERTION TOOLS

RELATED APPLICATIONS

The present application claims priority under 35 U.S.C. §119(e) to U.S. Provisional Patent Application No. 61/223,774 by Chuladatta Thenuwara et al., filed on Jul. 8, 2009, and entitled "LEAD INSERTION TOOLS," the contents of which are hereby incorporated by reference in their entirety.

BACKGROUND

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be at least partially implanted in the cochlea. The electrodes form a number of stimulation channels through which electrical stimulation pulses may be applied directly to auditory nerves within the cochlea. An audio signal may then be presented to a patient by translating the audio signal into a number of electrical stimulation pulses and applying the stimulation pulses directly to the auditory nerve within the cochlea via one or more of the electrodes.

The lead is often implanted within the scala tympani, one of the three parallel ducts that make up the spiral-shaped cochlea. Leads that are implanted in the scala tympani typically include several separately connected stimulating electrodes (or "electrode contacts") longitudinally disposed on a thin, elongate, and flexible carrier, thereby forming an electrode array of the lead. Such an electrode array of the lead is pushed into the scala tympani duct via a surgical opening made in the cochlea wall at or near the round window at the basal end of the duct.

During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one electrode contact site tends to selectively activate those spiral ganglion cells and their auditory nerve fibers that are closest to that contact site.

Hence, it is often desirable for the electrode contacts to be positioned as close to the ganglion cells as possible and/or to any other location (e.g., a mid-scalar location) as may serve a particular implementation. To this end, various leads have been developed that have resilient carriers configured to better conform to the shape of the scala tympani and/or other auditory structures.

Unfortunately, many conventional insertion tools used to insert leads into the cochlea are cumbersome and difficult to use. For example, it is often difficult to release a lead from an insertion tool once the lead has been inserted into the cochlea.

SUMMARY

An exemplary insertion tool configured to facilitate insertion of a lead having a plurality of electrodes disposed thereon into a bodily orifice includes a handle assembly configured to facilitate handling of the insertion tool, an insertion assembly coupled to the handle assembly and comprising a rigid holding tube configured to removably couple to a portion of the lead, and a release assembly disposed at least partially within the handle assembly and comprising a release button. The release assembly is configured to release the lead from the holding tube in response to user actuation of the release button.

An exemplary system configured to facilitate insertion of a lead having a plurality of electrodes disposed thereon at least partially into a bodily orifice includes a lead and an insertion tool. The lead includes a stimulation portion having a plurality of electrodes disposed thereon, a lead body configured to facilitate handling of the lead, and a jog portion configured to connect the lead body to the stimulation portion. The insertion tool includes a handle assembly, an insertion assembly coupled to the handle assembly and comprising a rigid holding tube having a receiving slot disposed therein that is configured to facilitate passage therethrough of the jog portion of the lead in order to facilitate removable coupling of the jog portion to the holding tube, and a release assembly disposed at least partially within the handle assembly and comprising a release button. The release assembly is configured to release the lead from the holding tube in response to user actuation of the release button.

An exemplary method of inserting a lead having a plurality of electrodes disposed thereon into a bodily orifice includes coupling a portion of the lead to a holding tube that is a part of an insertion tool, guiding the lead into the bodily orifice with the insertion tool, and actuating a release button that is a part of the insertion tool to release the lead from the holding tube.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Exemplary insertion tools, systems, and methods for inserting a lead into a bodily orifice are described herein. As used herein, the term "bodily orifice" refers to a duct of the cochlea, a surgically-made opening or incision (e.g., a cochleostomy or facial recess) within the patient, or any other location within the patient. For illustrative purposes only, it will be assumed in the examples given herein that the insertion tools, systems, and methods described herein may be used to insert at least a portion of a lead into a duct of the cochlea via a cochleostomy.

In some examples, an insertion tool includes a handle assembly, an insertion assembly, and a release assembly coupled one to another. The handle assembly is configured to facilitate handling of the insertion tool. The insertion assembly includes at least a rigid holding tube configured to removably couple to a proximal portion of a lead. The release assembly is disposed at least partially within the handle assembly and includes at least a release button. The release assembly is configured to release the lead from the holding tube in response to user actuation of the release button.

A number of advantages are associated with the insertion tools, systems, and methods described herein. For example, the insertion tools described herein may facilitate the insertion of a lead that is straight or slightly curved into a duct of the cochlea without the insertion tools being advanced into the facial recess. The insertion tools described herein may additionally or alternatively be used with either the right or left hand of a surgeon or other user and are configured to not obstruct the view of the user while inserting the lead into the cochlea. Moreover, the insertion tools described herein may facilitate one-handed release of a lead therefrom. These advantages will be described in more detail below.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
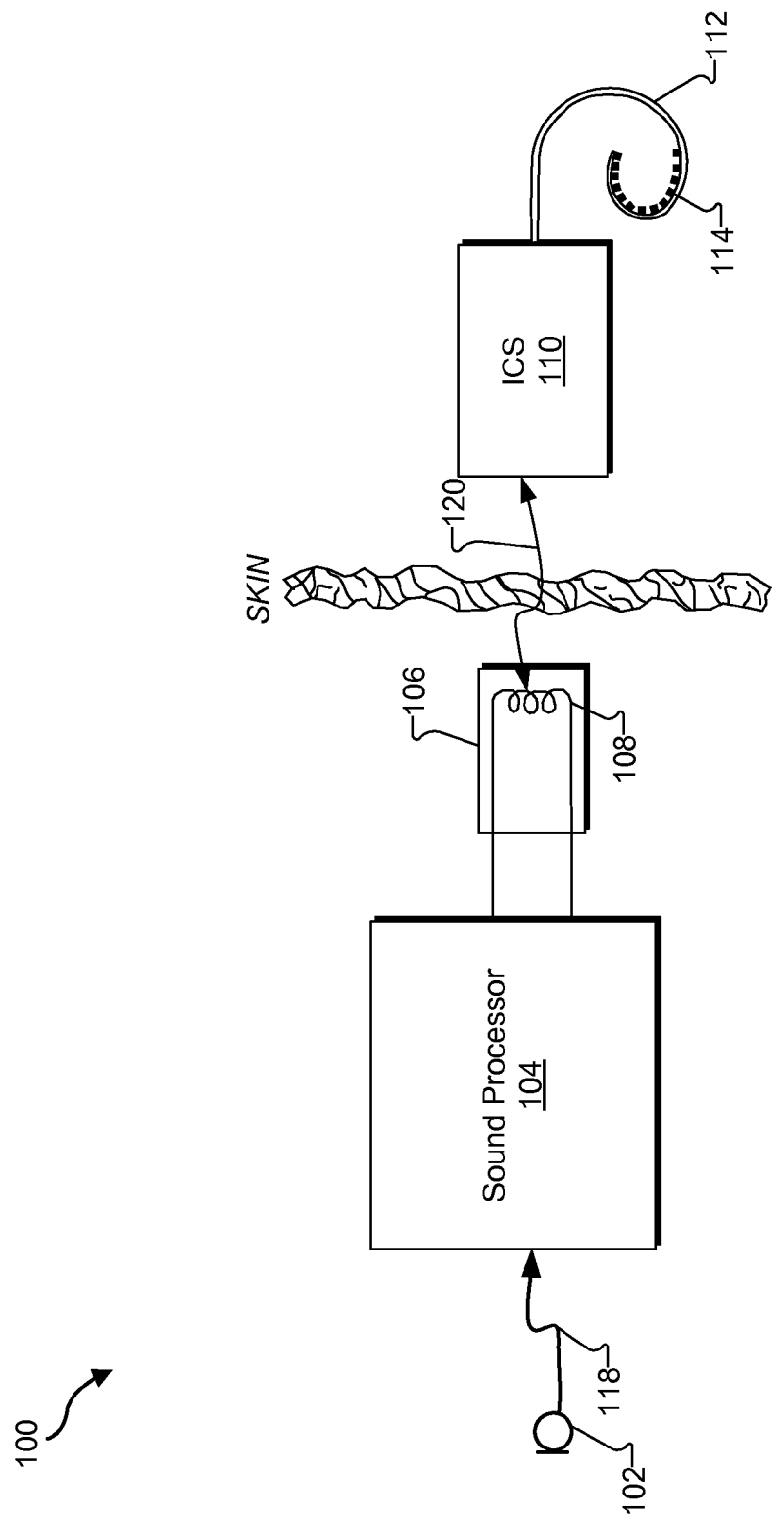
FIG. 1 illustrates an exemplary cochlear implant system according to principles described herein.

FIG. 1 illustrates an exemplary cochlear implant system 100. Cochlear implant system 100 may include a microphone 102, a sound processor 104, a headpiece 106 having a coil 108 disposed therein, an implantable cochlear stimulator ("ICS") 110, and a lead 112 with a plurality of electrodes 114 disposed thereon. Additional or alternative components may be included within cochlear implant system 100 as may serve a particular implementation.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 118, which may include a telemetry link, a wire, and/or any other suitable communication link.

Sound processor 104 is configured to direct implantable cochlear stimulator 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling implantable cochlear stimulator 110. Sound processor 104 may include or be implemented within a behind-the-ear ("BTE") unit, a portable speech processor ("PSP"), and/or any other sound processing unit as may serve a particular implementation. Exemplary components of sound processor 104 will be described in more detail below.

Sound processor 104 may be configured to transcutaneously transmit one or more control parameters and/or one or more power signals to implantable cochlear stimulator 110 with coil 108 by way of communication link 120. These control parameters may be configured to specify one or more stimulation parameters, operating parameters, and/or any other parameter as may serve a particular implementation.

Exemplary control parameters include, but are not limited to, volume control parameters, program selection parameters, operational state parameters (e.g., parameters that turn a sound processor and/or an implantable cochlear stimulator on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and back-end dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within implantable cochlear stimulator 110. In this manner, control parameters and power signals may be wirelessly transmitted between sound processor 104 and implantable cochlear stimulator 110 via communication link 120. It will be understood that data communication link 120 may include a bi-directional communication link and/or one or more dedicated uni-directional communication links. In some alternative embodiments, sound processor 104 and implantable cochlear stimulator 110 may be directly connected with one or more wires or the like.

Implantable cochlear stimulator 110 may be configured to generate electrical stimulation representative of an audio signal detected by microphone 102 in accordance with one or more stimulation parameters transmitted thereto by sound processor 104. Implantable cochlear stimulator 110 may be further configured to apply the electrical stimulation to one or more stimulation sites within the cochlea via one or more electrodes 114 disposed along lead 112.

To facilitate application of the electrical stimulation generated by implantable cochlear stimulator 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 2:
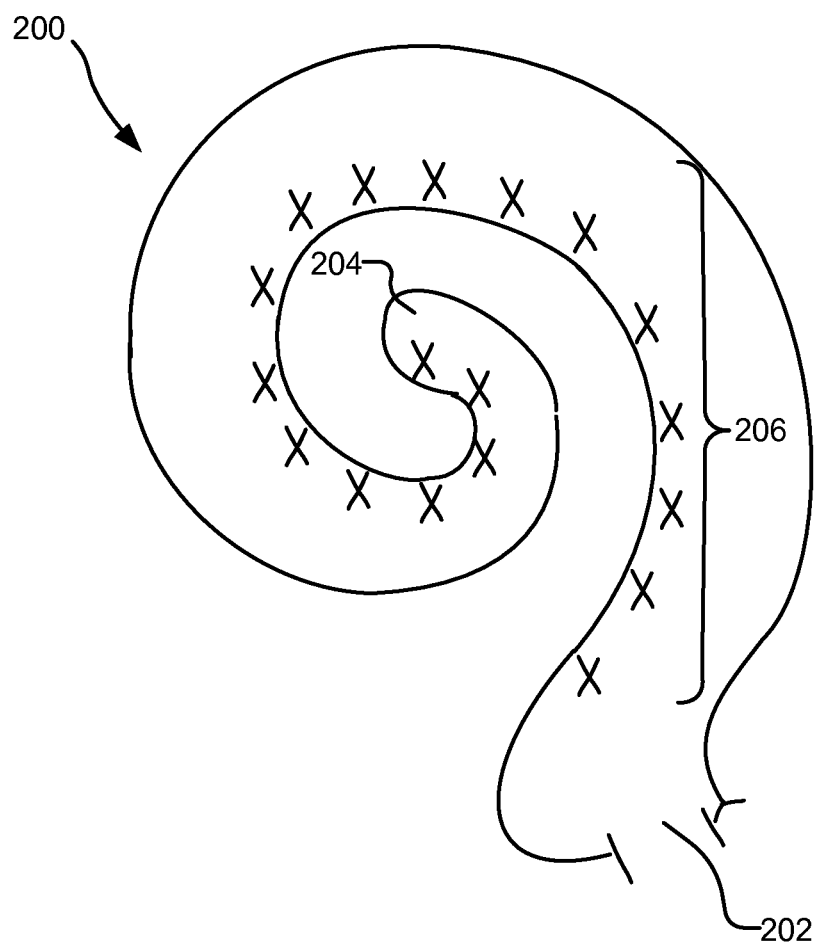
FIG. 2 illustrates a schematic structure of human cochlea.

FIG. 2 illustrates a schematic structure of the human cochlea 200 into which lead 112 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. System 100 may therefore be configured to apply electrical stimulation to different locations within the cochlea 200 (e.g., different locations along the auditory nerve tissue 206) to provide a sensation of hearing.

Figure 3:
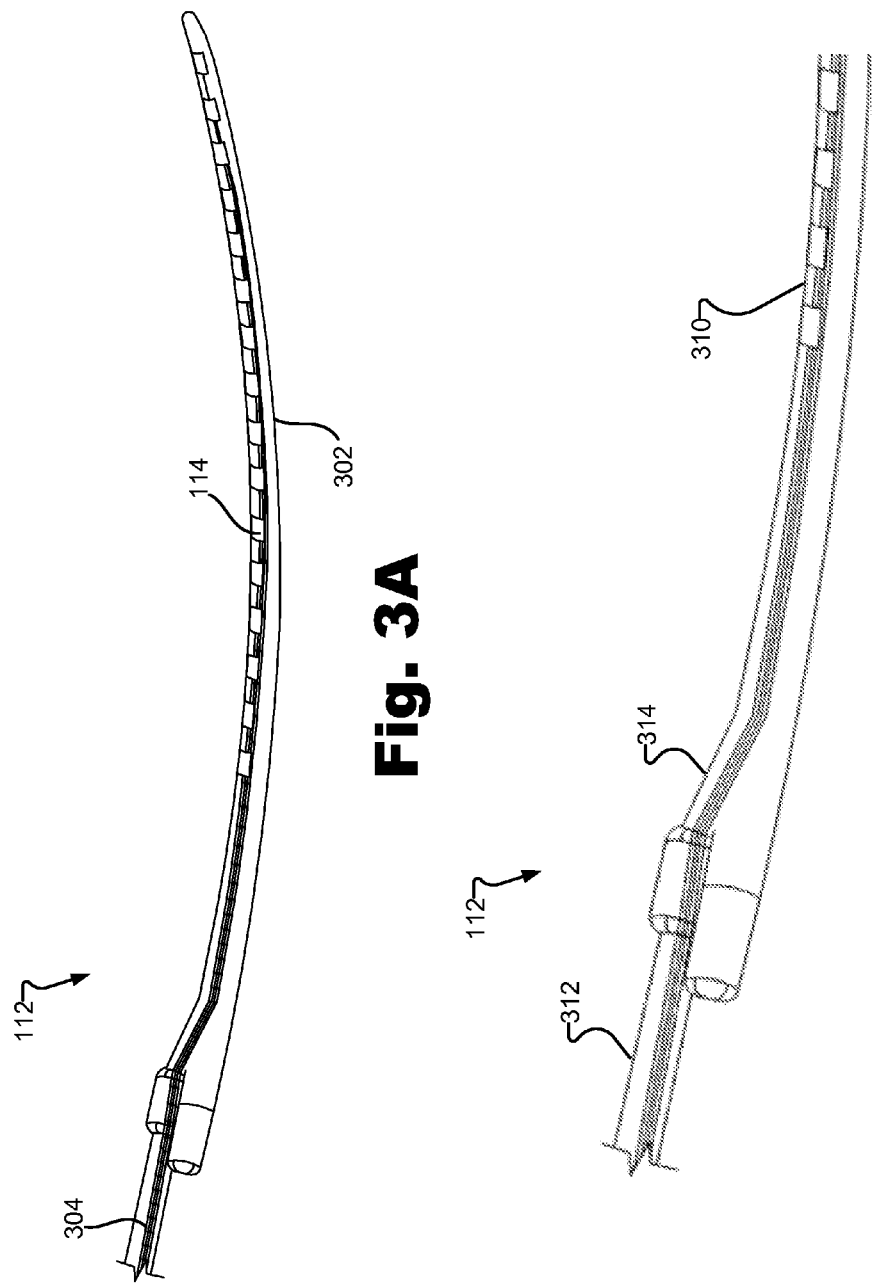
FIGS. 3A-3B illustrate an exemplary lead according to principles described herein.

FIGS. 3A-3B illustrate an exemplary lead 112 that may be used in connection with the systems and methods described herein. In some examples, lead 112 is referred to as a lateral wall lead because when inserted within a duct of the cochlea, electrodes 114 rest along the lateral wall of the cochlear duct. To this end, as shown in FIG. 3A, lead 112 may be slightly curved. Alternatively, lead 112 may be straight or of any other shape as may serve a particular implementation.

In some examples, lead 112 includes an elongate flexible carrier 302 having electrodes 114 disposed thereon that are connected to corresponding insulated wires 304. Elongate flexible carrier 302 may be made out of any suitable material such as, but not limited to, silicone rubber or plastic. In this manner, flexible carrier 302 may rest on the lateral wall of the cochlear duct by conforming to the shape of the cochlea when inserted within the cochlear duct.

As shown in FIG. 3A, a proximal end of carrier 302 is coupled to a lead body through which wires 304 pass. Wires 304 connect electrodes 114 to circuitry within implantable cochlear stimulator 110. Implantable cochlear stimulator 110 is thus able to make electrical connection with each of the electrode contacts 114 through one or more of the wires.

FIG. 3B illustrates a portion of lead 112 that facilitates loading of the lead 112 onto the insertion tools described herein. As shown in FIG. 3B, lead 112 may include a stimulation portion 310, a lead body 312, and a jog portion 314. Stimulation portion 310 may include the plurality of electrodes 114 shown in FIG. 3A disposed thereon. Lead body 312 may be configured to facilitate handling of the lead 112 by a surgeon or other user. Jog portion 314 may connect the lead body 312 to stimulation portion 310. As will be described in more detail below, jog portion 314 may be further configured to facilitate removable coupling of lead 112 to an insertion tool.

Figure 4:
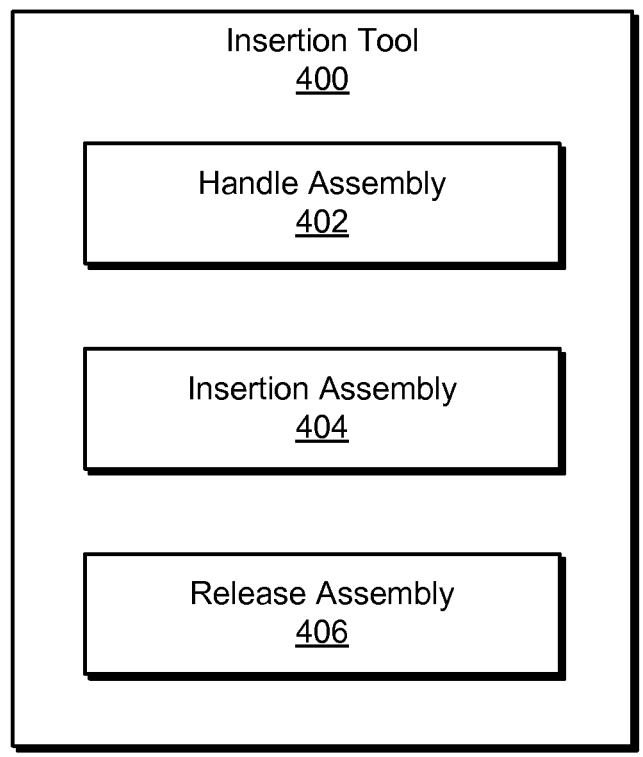
FIG. 4 is a block diagram of an exemplary insertion tool that may be used to insert a lead into a bodily orifice according to principles described herein.

FIG. 4 is a block diagram of an exemplary insertion tool 400 that may be used to insert lead 112 into a bodily orifice. As shown in FIG. 4, insertion tool 400 may include a handle assembly 402, an insertion assembly 404, and a release assembly 406. Each of the assemblies 402-406 may be coupled one to another and may include one or more components, as will be described in more detail below.

In some examples, handle assembly 402 may facilitate handling of insertion tool 400. For example, as will be described in more detail below, a surgeon or other user may grasp handle assembly 402 with one hand and use insertion tool 400 to insert lead 112 into a bodily orifice.

Insertion assembly 404 is coupled to handle assembly 402 and may be configured to removably couple to a proximal portion of lead 112. Exemplary configurations for facilitating such removable coupling will be described in more detail below.

Release assembly 406 may be disposed at least partially within handle assembly 402 and may be configured to release lead 112 from insertion assembly 404 in response to an action performed by a user thereof. For example, as will be described in more detail below, release assembly 406 may include a release button that may be actuated by a user to release lead 112 from insertion assembly 404.

Figure 5:
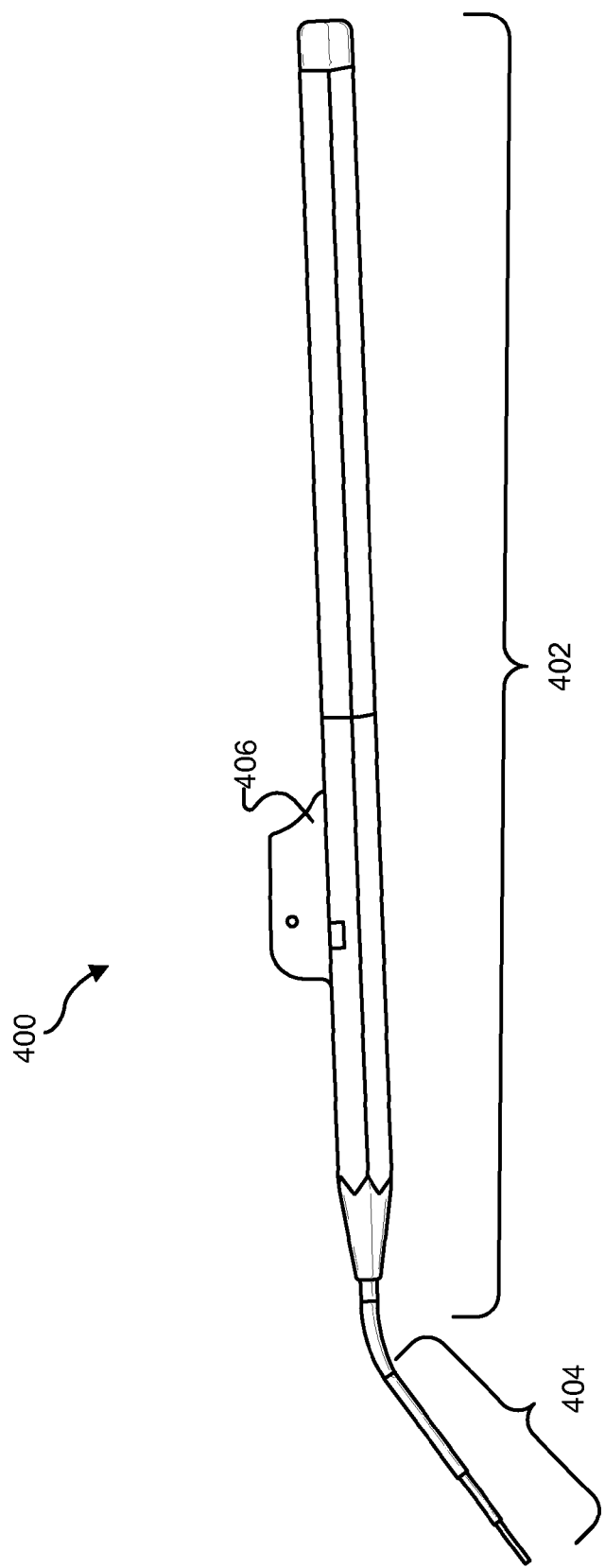
FIG. 5 is a perspective view of an exemplary insertion tool according to principles described herein.

FIG. 5 is a perspective view of insertion tool 400 including handle assembly 402, insertion assembly 404, and release assembly 406. As shown in FIG. 5, handle assembly 402 may include a generally elongate member configured to facilitate handling thereof by a user. Insertion assembly 404 may extend away from handle assembly 402 at an angle in order to facilitate insertion of lead 112 into a bodily orifice. A partial view of release assembly 406 is also shown in FIG. 5. As shown in FIG. 5, release assembly 406 may be disposed at least partially within handle assembly 406. Each of the assemblies 402-406 will now be described in more detail.

Figure 6:
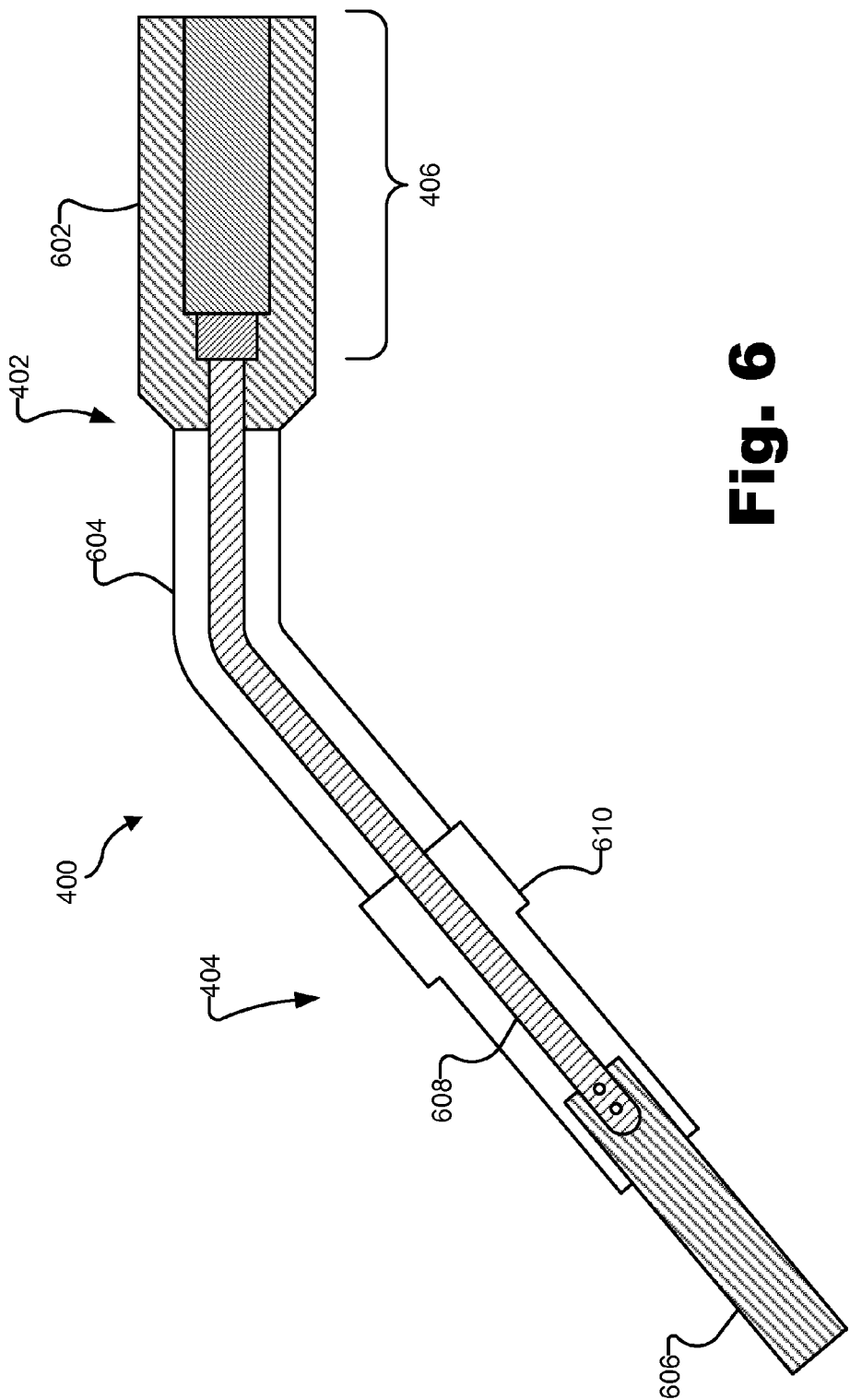
FIG. 6 is a cross-sectional side view of a portion of the insertion tool of FIG. 5 according to principles described herein.

FIG. 6 is a cross-sectional side view of a portion of insertion tool 400 that shows a number of exemplary components that may be included within handle assembly 402 and insertion assembly 404. It will be recognized that the components shown in FIG. 6 are merely illustrative of the many different components that may be included within handle assembly 402 and/or insertion assembly 404.

As shown in FIG. 6, handle assembly 402 may include a handle portion 602 coupled to a rigid handle tube 604. Handle portion 602 may be configured to facilitate handling of insertion tool 400 by a user and may house at least a portion of the release assembly 406. In some examples, handle portion 602 is generally elongate in shape and may include a lumen extending at least partially therethrough. In this manner, as will be described in more detail below, one or more components of insertion tool 400 may be disposed within handle portion 602. In some examples, handle portion 602 may have a hexagonal cross-section to facilitate optimal gripping thereof by a user. Handle portion 602 may alternatively have any other cross-sectional shape as may serve a particular implementation.

Handle tube 604 may be coupled to a distal end of handle portion 602. Handle tube 604 may be coupled to handle portion 602 in any suitable manner as may serve a particular implementation. For example, handle tube 604 may be welded, glued, or otherwise coupled to handle portion 602. Alternatively, handle tube 604 and handle portion 602 may be made out of a single mold. Handle tube 604 and/or handle portion 602 may be made out of any rigid material as may serve a particular implementation. For example, handle tube 604 and/or handle portion 602 may be made out of stainless steel, titanium, a rigid plastic, and/or any other rigid material as may serve a particular implementation.

In some examples, handle tube 604 includes a lumen extending therethrough and in communication with the lumen of handle portion 602. In this manner, as will be described in more detail below, one or more components of insertion tool 400 may pass through the lumen of handle tube 604 and the lumen of handle portion 602.

As shown in FIG. 6, handle tube 604 may include a curved portion such that a distal portion of handle tube 604 extends away from handle portion 602 at a predefined angle. The angle at which handle tube 604 extends from handle portion 602 may be defined to be any angle as may serve a particular implementation.

In some examples, handle tube 604 may be coupled to at least one component of insertion assembly 404. Such coupling will be described in more detail below.

Insertion assembly 404, as shown in FIG. 6, may include a holding tube 606, a flexible tube 608, and a guide tube 610. As will be described in more detail below, flexible tube 608 may be coupled to a proximal portion of holding tube 606 and extend through a lumen of guide tube 610, a lumen of handle tube 604, and a lumen of handle portion 602 before being coupled to a component of release assembly 406. Flexible tube 608 may be made out of any suitable flexible material as may serve a particular implementation. For example flexible tube 608 may be made out of polytetrafluoroethylene ("PTFE") and/or any suitable material with sufficient flexibility to move back and forth through the curved portion of handle tube 604.

Figure 7:
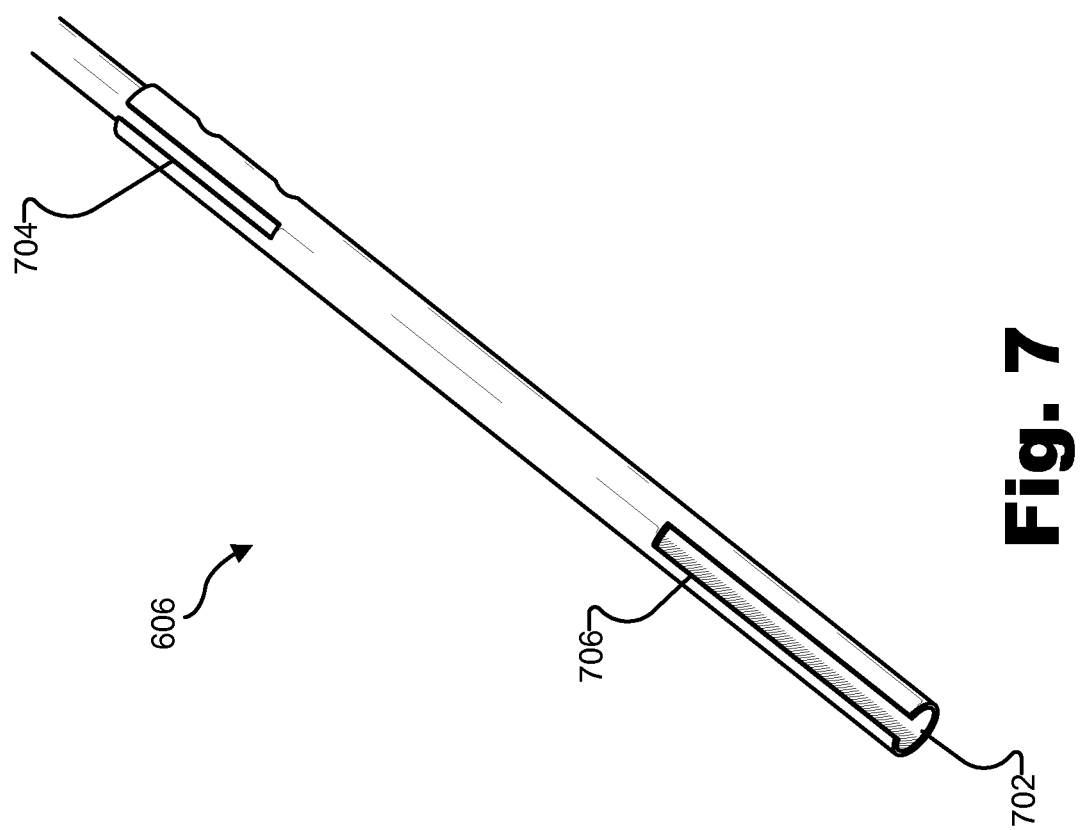
FIG. 7 is a perspective view of a holding tube according to principles described herein.

FIG. 7 is a perspective view of holding tube 606. As shown in FIG. 7, holding tube 606 may include an elongate member having a receiving slot 702 extending along a distal portion thereof and an outwardly extending key member 704. Holding tube 606 may additionally include a lumen 706 extending therethrough. As will be described in more detail below, lead 112 and/or one or more components of release assembly 406 may be at least partially disposed within lumen 706 of holding tube 606.

Holding tube 606 may be made out of any rigid material as may serve a particular implementation. For example, holding tube 606 may be made out of stainless steel, titanium, a rigid plastic, and/or any other rigid material as may serve a particular implementation. The rigidity of holding tube 606 may prevent buckling during insertion of lead 112 into a bodily orifice.

Receiving slot 702 is configured to facilitate removable coupling of lead 112 to holding tube 606. For example, as will be described in more detail below, jog portion 314 of lead 112 may fit within receiving slot 702. In this manner, lead 112 may be advanced partially into lumen 706 of holding tube 606 until a portion of lead 112 makes contact with a stationary backstop member disposed within lumen 706 of holding tube 606. An exemplary backstop member that may be disposed within lumen 706 of holding tube 606 will be described in more detail below.

Outwardly extending key member 704 may be dimensioned to fit within a corresponding slot included within guide tube 610. Key member 704 may facilitate longitudinal movement of holding tube 606 within guide tube 610, as will be described in more detail below.

Figure 8:
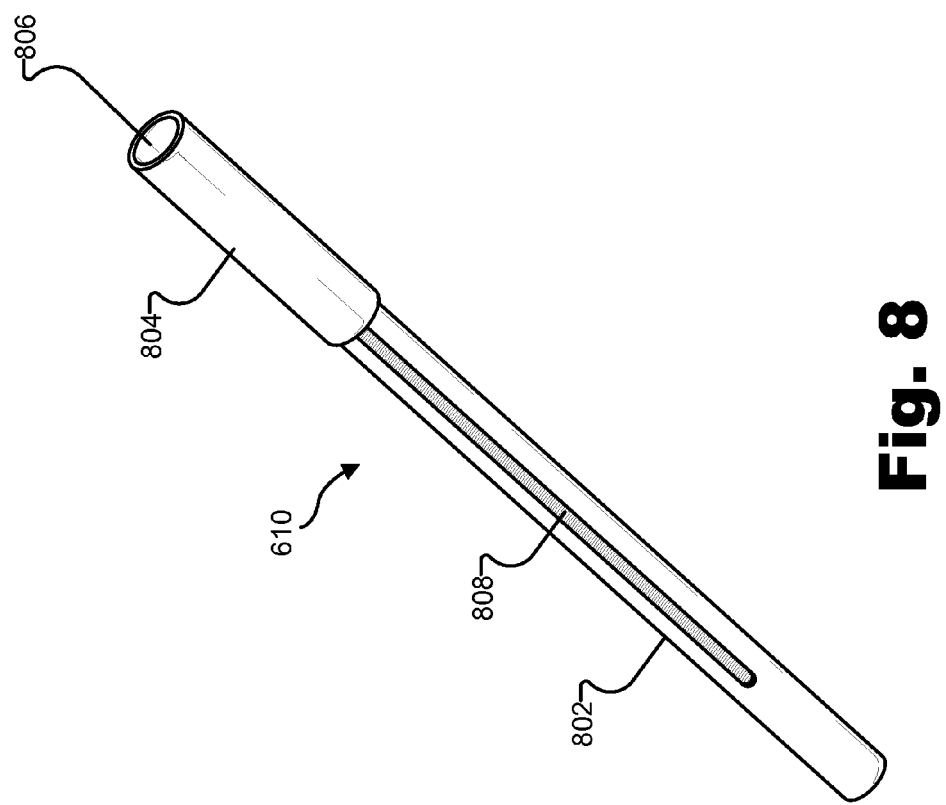
FIG. 8 is a perspective view of a guide tube according to principles described herein.

FIG. 8 is a perspective view of guide tube 610. As shown in FIG. 8, guide tube 610 includes a slotted tube 802 coupled to a sleeve 804. Slotted tube 802 and sleeve 804 may be coupled one to another in any suitable manner as may serve a particular implementation. For example, slotted tube 802 and sleeve 804 may be welded, glued, or otherwise coupled one to another. Alternatively, slotted tube 802 and sleeve 804 may be made out of a single mold. Slotted tube 802 and/or sleeve 804 may be made out of any suitable material as may serve a particular implementation. For example, slotted tube 802 and/or sleeve 804 may be made out of stainless steel, titanium, a rigid plastic, and/or any other material as may serve a particular implementation.

As shown in FIG. 8, guide tube 610 includes a lumen 806 extending through both slotted tube 802 and sleeve 804. As will be described in more detail below, lumen 806 may facilitate the passage therethrough of holding tube 606 and flexible tube 608.

Slotted tube 802 may include a slot 808 partially extending along a length thereof. As will be described in more detail below, key member 704 of holding tube 606 may fit within slot 808 such that holding tube 606 may move longitudinally within lumen 806 of guide tube 610.

As shown in FIG. 8, sleeve 804 may be coupled to handle tube 604 with an interference fit. For example, handle tube 604 may have a circumference slightly smaller than that of the circumference of sleeve 804. In this manner, a distal portion of handle tube may be fit within guide tube 610 such that guide tube 610 and handle tube 604 are coupled one to another without the use of a permanent affixation technique or device. The interference fit of handle tube 604 within guide tube 610 may allow guide tube 610 to be rotatable with respect to handle tube 604. By rotating guide tube 610, a surgeon or other user thereof may orient insertion assembly 404 in an optimal radial direction.

Figure 9:
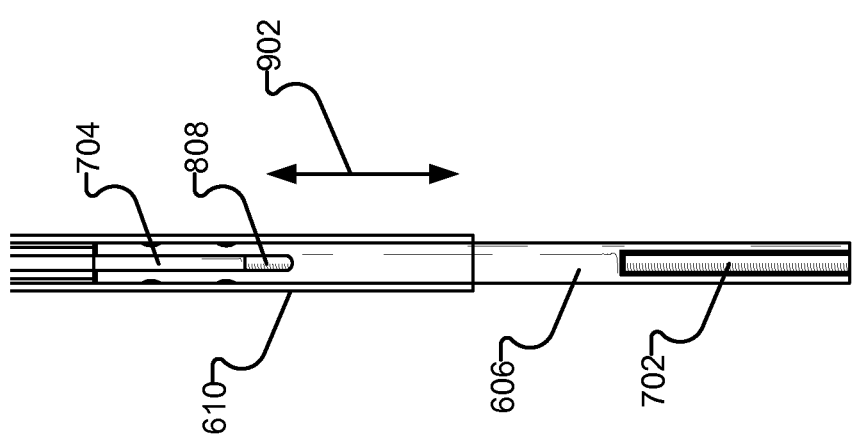
FIG. 9 is a top view of a holding tube and a guide tube coupled one to another according to principles described herein.

FIG. 9 is a top view of holding tube 606 and guide tube 610 coupled one to another. As shown in FIG. 9, key member 704 of holding tube 606 is disposed within slot 808 of guide tube 610. In this manner, holding tube 606 may move back and forth longitudinally within holding tube 610, as indicated by arrow 902. With key member 704 disposed within slot 808, a rotation of guide tube 610 may cause holding tube 606 to concurrently rotate in a similar manner, thus providing a user thereof with the ability to optimally orient holding tube 606 and a lead 112 disposed therein.

Figure 10:
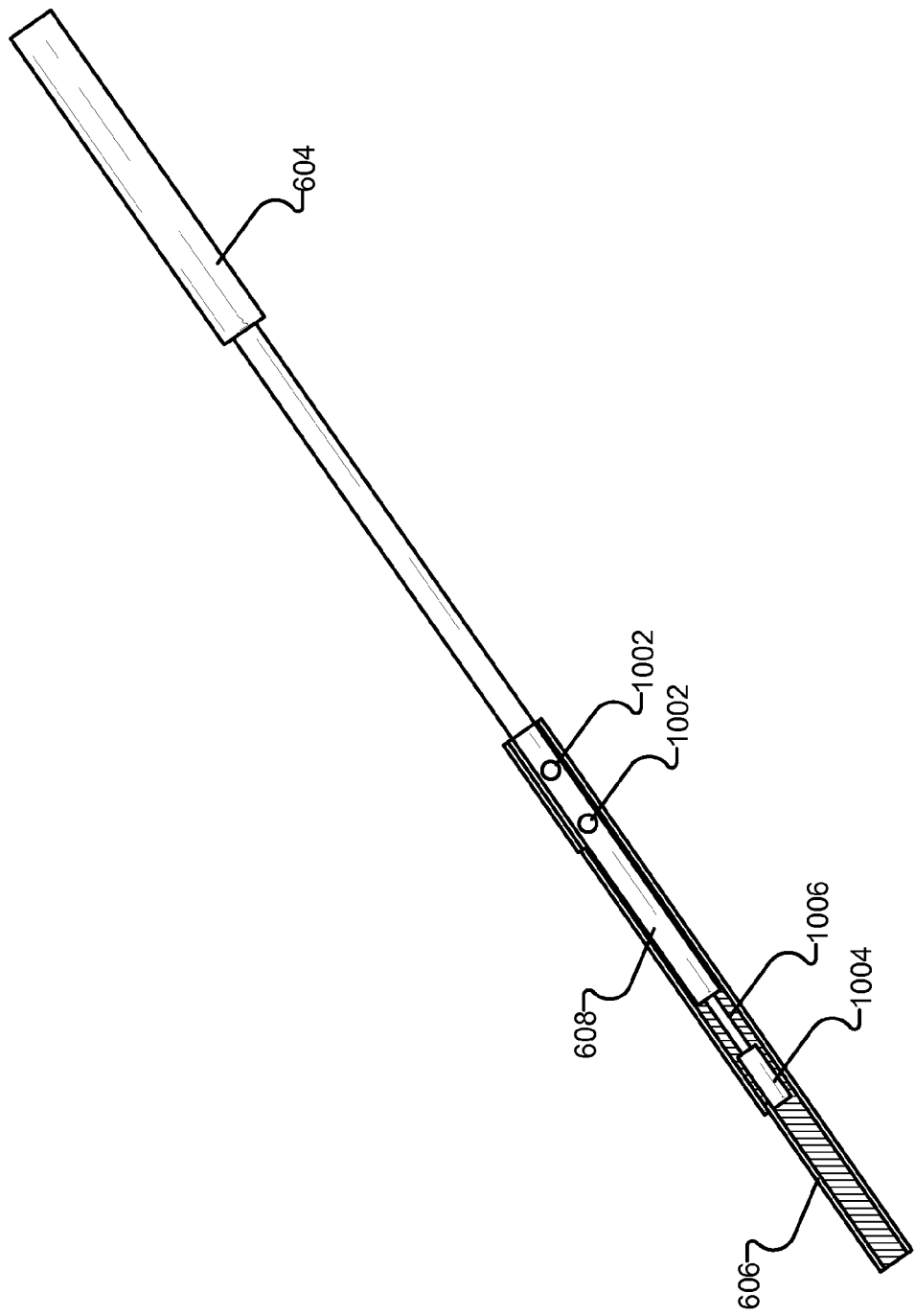
FIG. 10 is a perspective side view of a portion of an insertion tool that shows a flexible tube coupled to a holding tube according to principles described herein.

FIG. 10 is a perspective side view of a portion of insertion tool 400 that shows flexible tube 608 coupled to holding tube 606. As shown in FIG. 10, flexible tube 608 may be inserted within holding tube 606 and affixed thereto with one or more affixation devices 1002. Such affixation devices 1002 may include one or more screws, anchors, and/or any other affixation devices as may serve a particular implementation. Additionally or alternatively, glue or any other adhesive may be used to couple flexible tube 608 to holding tube 606. With flexible tube 608 coupled to holding tube 606 as shown in FIG. 10, movement (e.g., retraction) of flexible tube 608 may result in a corresponding movement of holding tube 606. In this manner, as will be described in more detail below, holding tube 606 may be retracted within guide tube 610 in order to release lead 112 therefrom.

FIG. 10 also shows a backstop member 1004 and a wire 1006 affixed to backstop member 1004. As shown in FIG. 10, backstop member 1004 is at least partially disposed within the lumen of holding tube 606. As will be described in more detail below, wire 1006 may pass through the lumen of flexible tube 608 and handle tube 604 until it is affixed permanently at a proximal end to an end block (described in more detail below) within handle portion 602. In this manner, wire 1006 may maintain backstop member 1004 in a stationary position. Wire 1006 may be made out of any suitable material as may serve a particular implementation. For example, wire 1006 may be made out of Nitinol.

As will be described in more detail below, backstop member 1004 may facilitate proper positioning of lead 112 within holding tube 606. Backstop member 1004 may further facilitate release of lead 112 from holding tube 606. Both backstop member 1004 and wire 1006 are included within release assembly 406 and will be described in more detail below.

Figure 11:
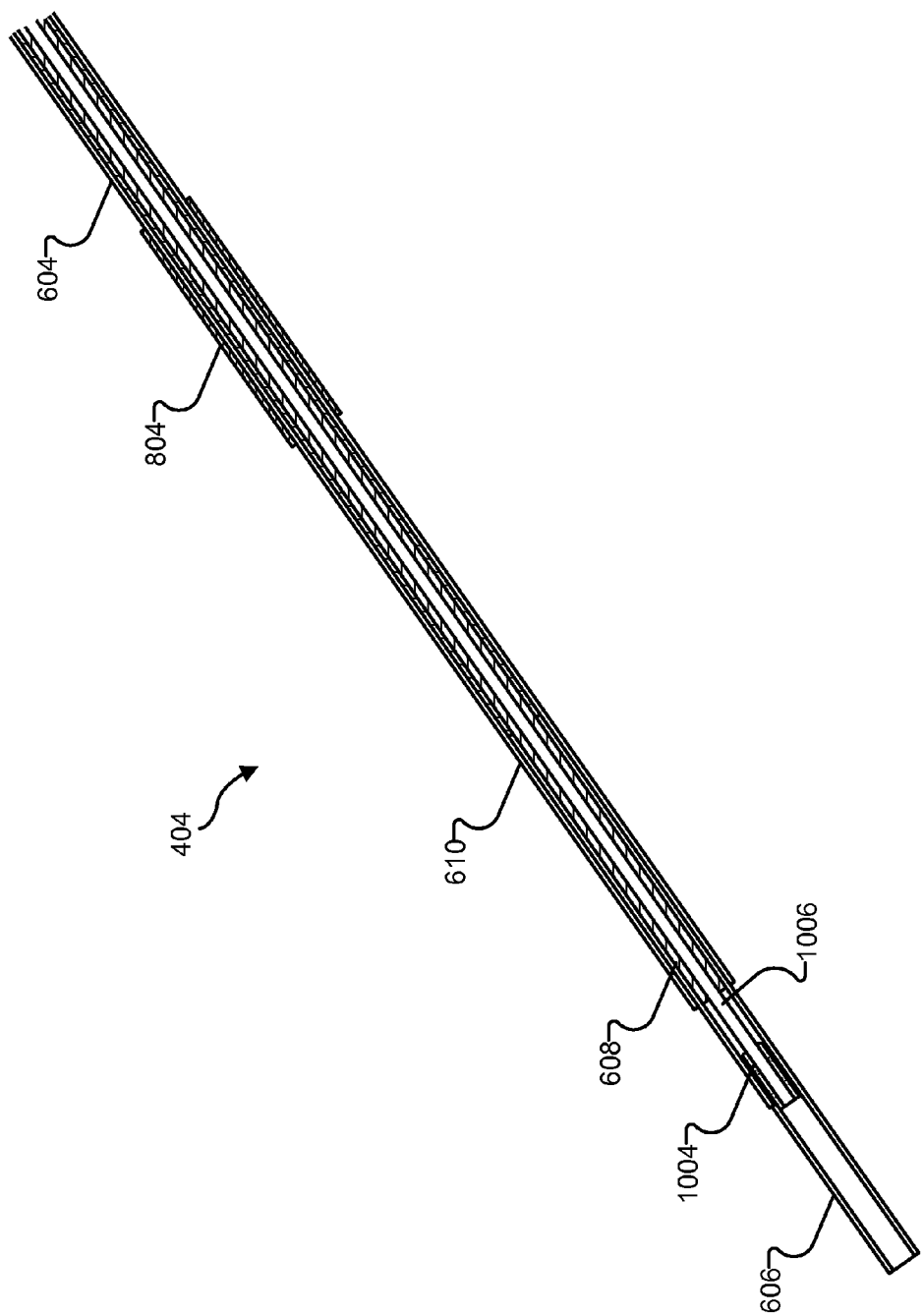
FIG. 11 is a cross-sectional top view of an insertion assembly according to principles described herein.

FIG. 11 is a cross-sectional top view of insertion assembly 404 and shows backstop member 1004 and wire 1006 disposed therein. FIG. 11 shows a distal portion of flexible tube 608 disposed within and coupled to holding tube 606 and that both flexible tube 608 and holding tube 606 are disposed within a lumen of guide tube 610. FIG. 11 also shows handle tube 604 disposed within and coupled to sleeve 804 of guide tube 610.

Figure 12:
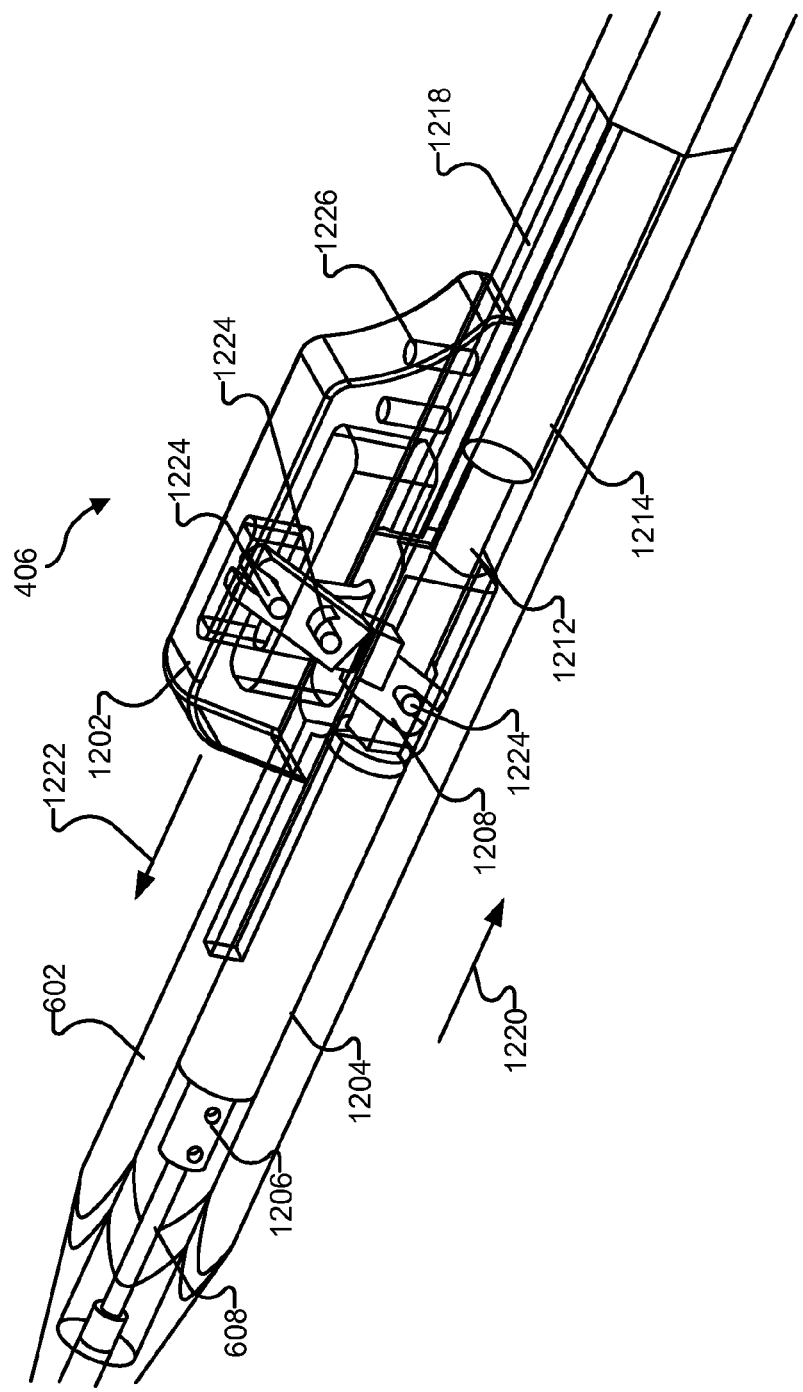
FIG. 12 is a perspective wireframe view of various components included within a release assembly according to principles described herein.
Figure 13:
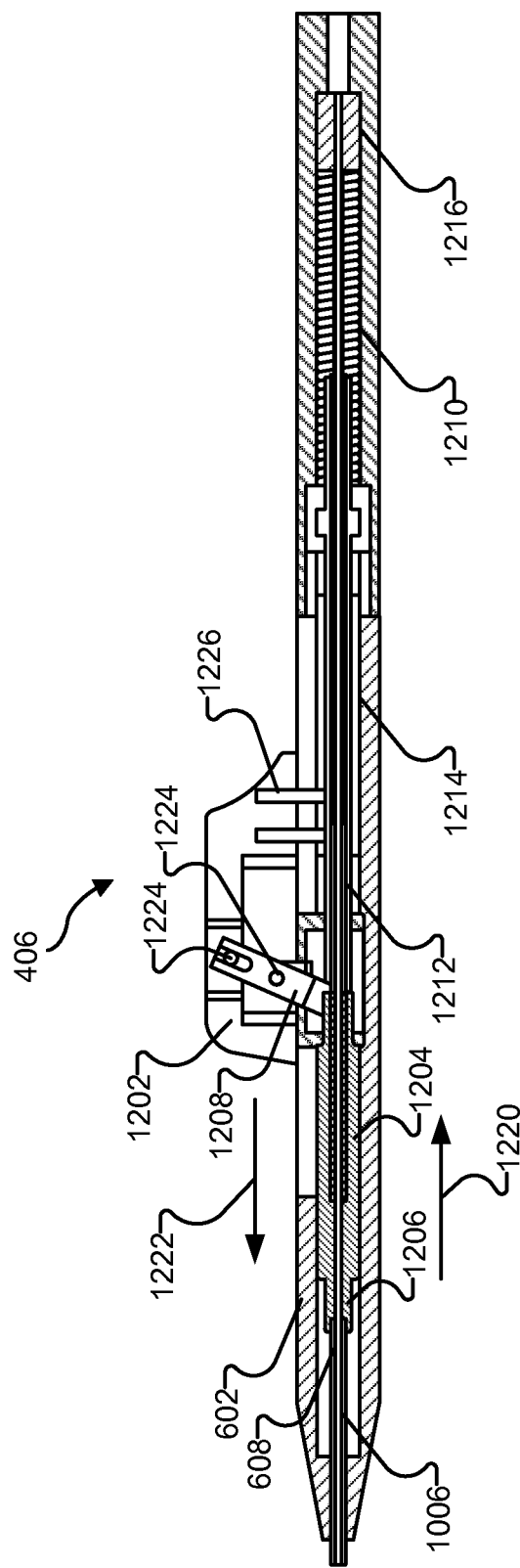
FIG. 13 is a cross-sectional side view of the components shown in FIG. 12 according to principles described herein.

FIG. 12 is a perspective wireframe view of various components included within release assembly 406. FIG. 13 is a cross-sectional side view of the components shown in FIG. 12. As shown in FIGS. 12-13, release assembly 406 may include a release button 1202, a plunger 1204, a plunger connecting member 1206, a lever 1208, a spring 1210, a spring connecting member 1212, a spring housing member 1214, and an end block 1216. Each of these components may be located at least partially within handle assembly 402 (e.g., disposed within a lumen of handle portion 602) and will now be described in more detail.

As shown in FIGS. 12-13, flexible tube 608 is configured to be coupled to plunger connecting member 1206. Flexible tube 608 may be connected to plunger connecting member 1206 in any suitable manner as may serve a particular implementation. For example, flexible tube 608 may be glued, screwed, or otherwise coupled to plunger connecting member 1206. Plunger connecting member 1206 is in turn coupled to plunger 1204. Plunger connecting member 1206 may be coupled to plunger 1204 in any suitable manner. For example, plunger connecting member 1206 may be welded, glued, or otherwise coupled to plunger 1204. Alternatively, plunger connecting member 1206 and plunger 1204 may be made out of a single mold.

In some examples, plunger connecting member 1206 may be rotatable with respect to plunger 1204. This rotation capability of plunger connecting member 1206 may allow flexible tube 608 and holding tube 606 to concurrently rotate in response to a rotation of guide tube 610. As described above, rotation of holding tube 606 may facilitate customizable orientation of lead 112 by a user of insertion tool 400.

In some alternative embodiments, flexible tube 608 may be coupled directly to plunger 1204. In such embodiments, the need for plunger connecting member 1206 is obviated.

As shown in FIGS. 12-13, plunger 1204 may include an elongate member disposed within the lumen of handle portion 602. A distal end of plunger 1204 is coupled to flexible tube 608 via plunger connecting member 1206, as described previously. A proximal end of plunger 1204 may be coupled to spring connecting member 1212, which in turn is coupled to spring 1210. A proximal end of spring 1210 is coupled to stationary end block 1216. As will be described in more detail below, compression of spring 1210 may cause plunger 1204 to retract in a direction indicated by arrow 1220. Retraction of plunger 1204 may cause flexible tube 608 and holding tube 606 to also retract. In some examples, retraction of flexible tube 608 and holding tube 606 may cause lead 112 to be released from holding tube 606, as will be explained in more detail below.

Release button 1202 may protrude from handle portion 602, as shown in FIGS. 12-13. To this end, handle portion 602 may include a slot 1218 extending at least partially along the length thereof through which release button 1202 may protrude. Release button 1202 may be coupled to plunger 1204 in any suitable manner that facilitates retraction of plunger 1204 in the direction of arrow 1220 in response to user actuation of release button 1202. For example, a lever 1208 may couple release button 1202 to plunger 1204. As shown in FIGS. 12-13, one or more horizontally extending pins 1224 may be coupled to release button 1202 and/or plunger 1204 in order to facilitate coupling lever 1208 to release button 1202 and plunger 1204.

In some examples, a user may advance (e.g., push) release button 1202 in a direction indicated by arrow 1222, which direction is substantially parallel to a longitudinal axis of handle portion 602. This movement may cause plunger 1204 to retract in the direction indicated by arrow 1220. Retraction of plunger 1204 may cause flexible tube 608 and holding tube 606 to also retract, thereby releasing lead 112 from holding tube 606. The advancement distance of release button 1202 required to cause plunger 1204 to retract may be any suitable distance as may serve a particular implementation. In some examples, the advancement distance is small enough such that the user does not have to reposition his hand relative to the handle portion 602 in order to effectuate the retraction of plunger 1204.

It will be recognized that release button 1202 may be configured to be alternatively actuated to release lead 112 from holding tube 606 in any suitable manner as may serve a particular implementation. For example, release button 1202 may be retracted or pulled back in a direction opposite that of arrow 1222, depressed, or otherwise actuated as may serve a particular implementation.

The movement of release button 1202 may cause spring 1210 to compress. Hence, when the user releases (i.e., lets go of) release button 1202, spring 1210 may automatically assume its natural uncompressed state. This action of spring 1210 causes plunger 1204 to also assume its natural non-retracted state and return release button 1202 to its original, unactuated position.

To facilitate coupling of spring 1210 to plunger 1204, release assembly 406 may further include spring connecting member 1212 and spring housing member 1214. Spring connecting member 1212 is configured to couple plunger 1204 to spring 1210 in any suitable manner as may serve a particular implementation. Spring housing member 1214 may at least partially house spring 1210 and/or spring connecting member 1212. One or more posts 1226 may be provided to anchor spring connecting member 1212 to handle portion 602 and/or release button 1202.

End block 1216 may be made out of any suitable material as may serve a particular implementation and is configured to be stationary within handle portion 602. As described above, a proximal end of spring 1210 may be coupled to end block 1216. FIG. 13 further illustrates that a proximal end of wire 1006 may be coupled (e.g., welded, etc.) to end block 1216. In this manner, wire 1006 may remain stationary with respect to flexible tube 608 and holding tube 606. As described above, wire 1006 is affixed to backstop member 1004 at a distal end. Hence, backstop member 1004 may also be stationary with respect to flexible tube 608 and holding tube 606 to facilitate release of lead 112 from holding tube 606.

Figure 14:
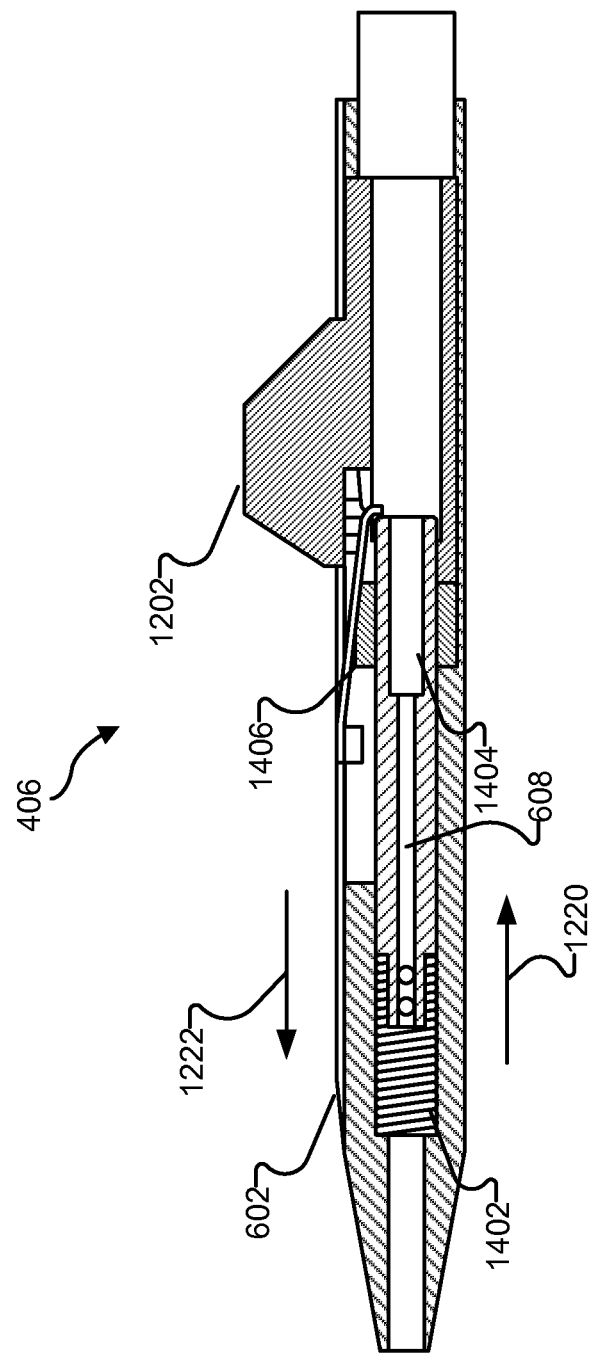
FIGS. 14-15 illustrate a number of components that may be included within an alternative configuration of a release assembly according to principles described herein.
Figure 15:
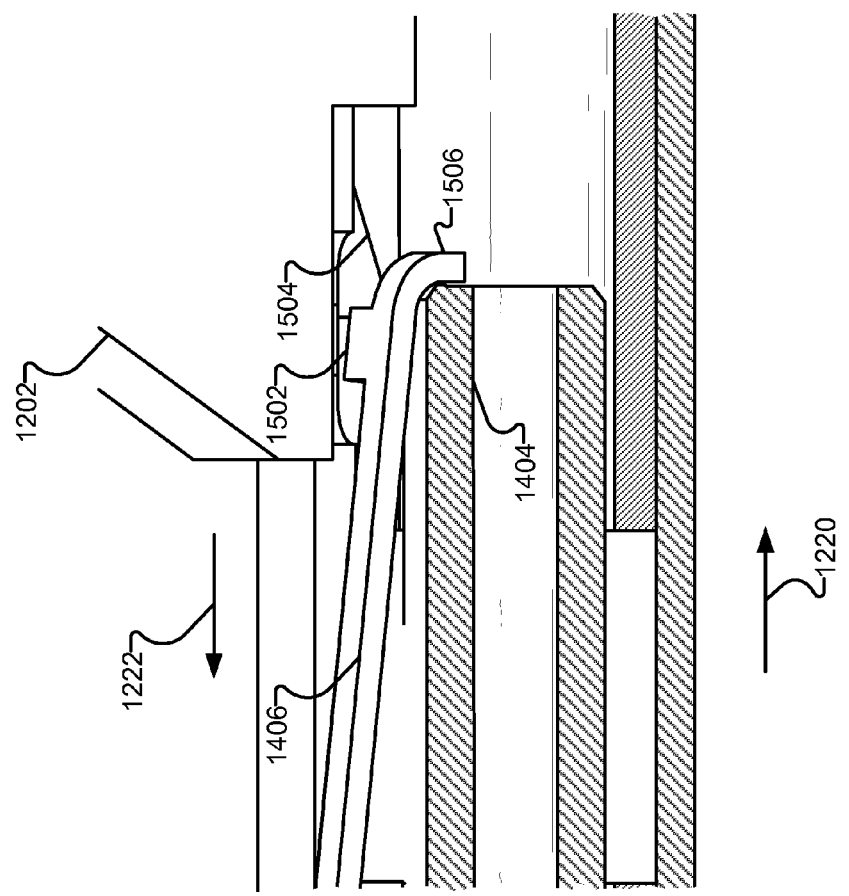

FIGS. 14-15 illustrate a number of components that may be included within an alternative configuration of release assembly 406. As shown in FIG. 14, release assembly may alternatively include a spring 1402 disposed within a distal portion of handle portion 602 and coupled to a spring-loaded plunger 1404. Plunger 1404 may be coupled to flexible tube 608 as described above in connection with plunger 1204.

A leaf spring 1406 may also be included to maintain spring 1402 in a compressed state and plunger 1404 in a distal position in the absence of user actuation of release button 1202. As shown in more detail in FIG. 15, leaf spring 1406 may include a wing member 1502 aligned with a tapered portion 1504 of release button 1202. In this manner, as release button 1202 is pushed or otherwise advanced in the direction indicated by arrow 1222, tapered portion 1504 lifts leaf spring 1406, thereby freeing spring 1402 to decompress (e.g., elongate) and retract plunger 1404 in a direction indicated by arrow 1220. The retraction of plunger 1404 may cause flexible tube 608 and holding tube 606 to retract (e.g., to release lead 112 from holding tube 606).

It will be recognized that release assembly 406 may additionally or alternatively include any other component configured to release lead 112 from holding tube 606 by causing holding tube 606 to retract in response to an action performed by a user of insertion tool 400.

Figure 16:
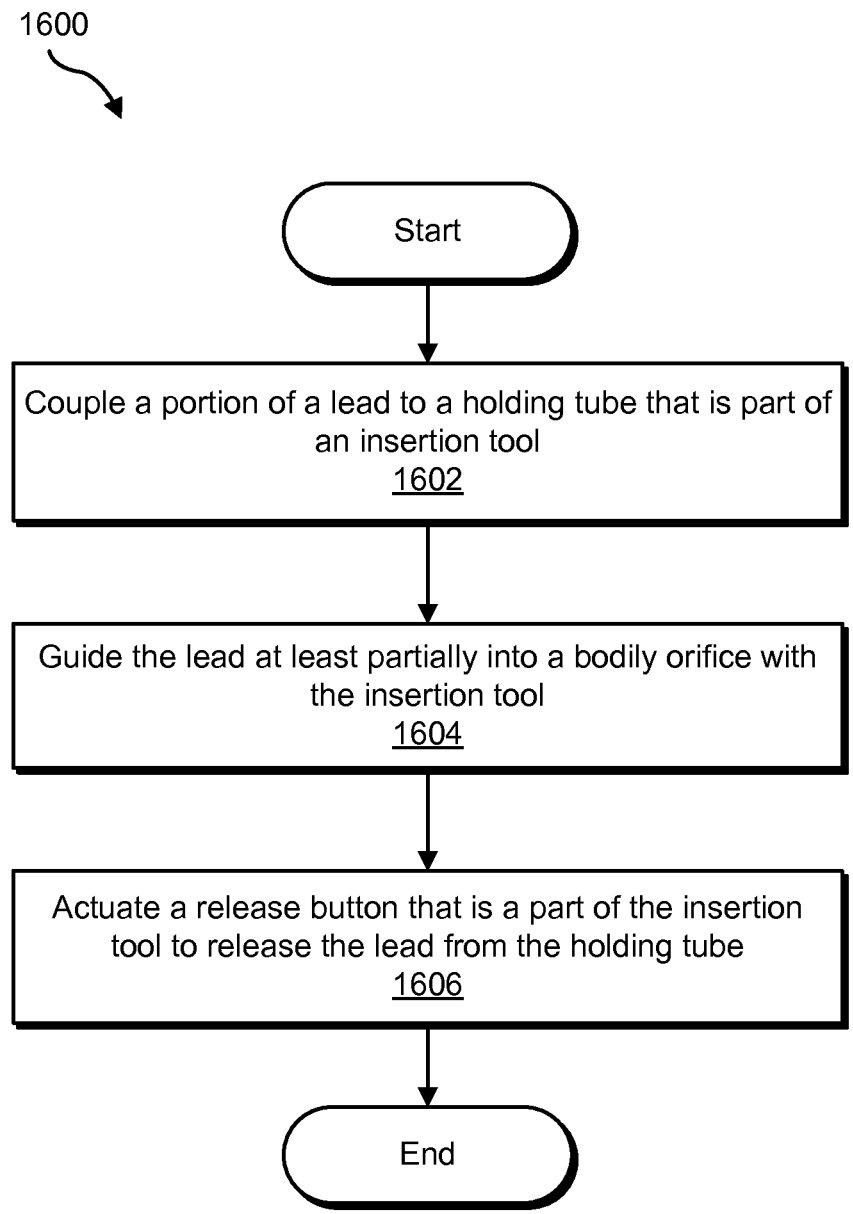
FIG. 16 illustrates an exemplary method of inserting a lead into a bodily orifice according to principles described herein.

FIG. 16 illustrates an exemplary method 1600 of inserting a lead into a bodily orifice. While FIG. 16 illustrates exemplary steps according to one embodiment, other embodiments may omit, add to, reorder, and/or modify any of the steps shown in FIG. 16.

Figure 17:
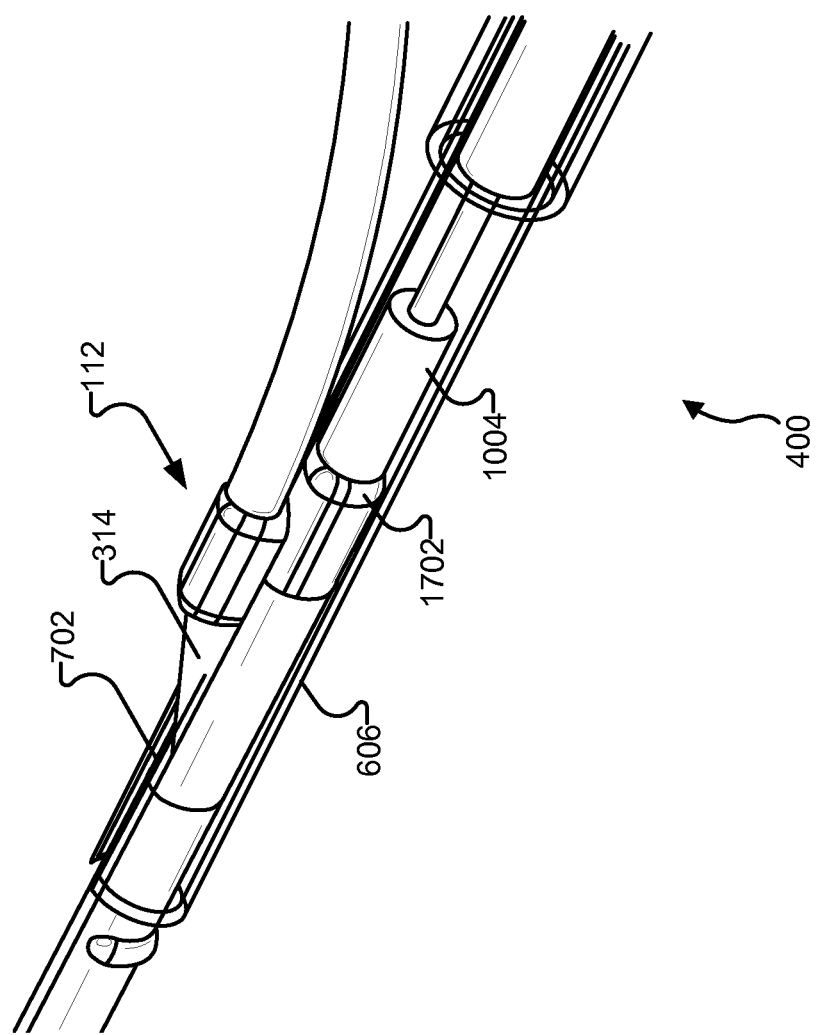
FIG. 17 shows an exemplary configuration wherein a lead is coupled to a holding tube of an insertion tool according to principles described herein.

In step 1602, a portion of a lead is coupled to a holding tube that is part of an insertion tool. The lead may be coupled to the holding tube in any of the ways described herein. For example, FIG. 17 shows an exemplary configuration wherein lead 112 is coupled to holding tube 606 of insertion tool 400. As shown in FIG. 17, jog portion 314 of lead 112 is configured to fit within receiving slot 702 of holding tube 606. A user may position lead 112 such that jog portion 314 is located within receiving slot 702 and advance lead 112 into the lumen of holding tube 606 until a proximal end 1702 of jog portion 314 comes into contact with stationary backstop member 1004. In some examples, backstop member 1004 may be positioned within holding tube 606 such that when jog portion 314 is in contact with backstop member 1004, lead 112 may be prevented from being removed through receiving slot 702.

Returning to FIG. 16, in step 1604, the lead is guided at least partially into a bodily orifice with the insertion tool. The lead may be guided into the bodily orifice in any suitable manner. For example, a user may grasp handle portion 602 of handle assembly 402 with one hand and guide stimulation portion 310 of lead 112 at least partially into the bodily orifice.

Figure 18:
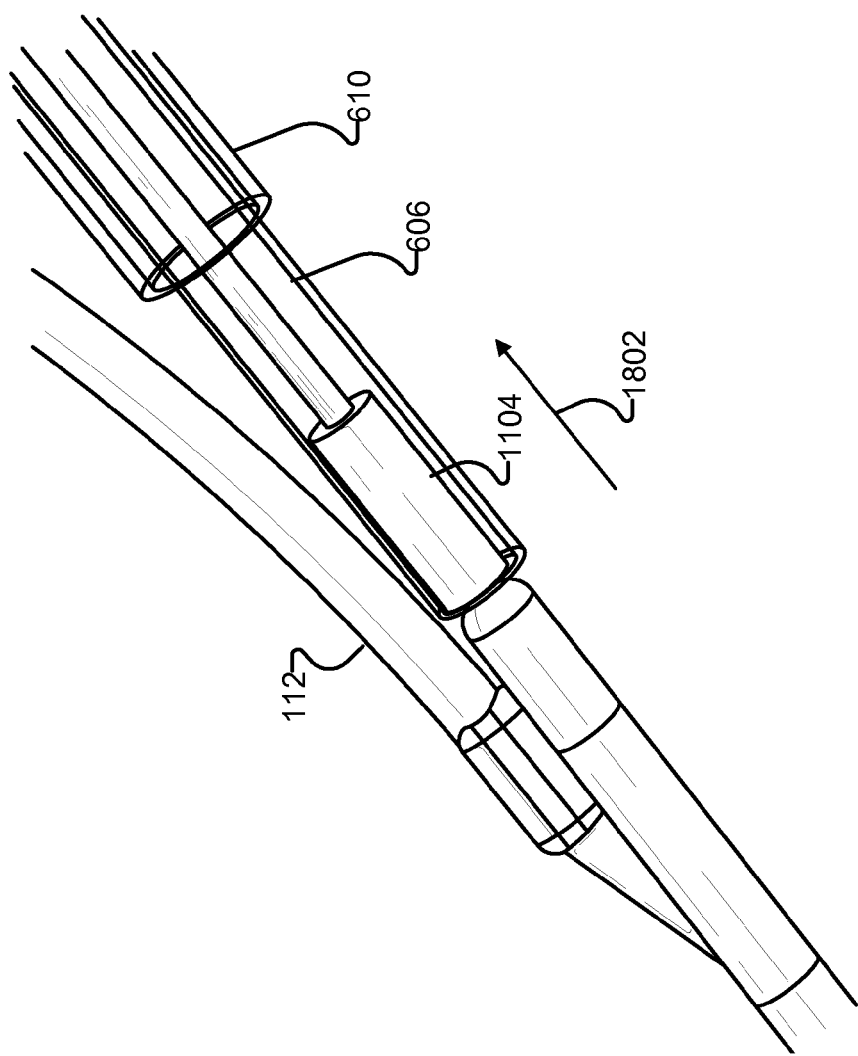
FIG. 18 shows a lead after it has been released from a holding tube according to principles described herein.

In step 1606, a release button is actuated that is a part of the insertion tool to release the lead from the holding tube. The release button may be actuated and the lead may be released from the holding tube in any suitable manner, such as described herein. For example, FIG. 18 shows lead 112 after it has been released from holding tube 606. As shown, user actuation of release button 1202 may cause holding tube 606 to retract within guide tube 610 in a direction indicated by arrow 1802 while backstop member 1104 retains lead 112 in place. As a result, lead 112 is exposed and released from holding tube 606.

The insertion tools described herein (e.g., insertion tool 400) may be configured to facilitate single-handed insertion of a lead into a bodily orifice. For example, a user may grasp handle portion 602 of insertion tool 400 with a single hand and guide lead 112 into the cochlear duct. Once lead 112 has been suitably positioned, the user may release lead 112 from insertion tool 400 with the same hand by actuating release button 1202 with the thumb or forefinger. This release of the lead 112 may be performed without substantially repositioning insertion tool 400 within the user's hand. In this manner, insertion tool 400 may provide a stable platform for the insertion of lead 112 and minimize trauma to the cochlea that may occur during the insertion procedure.

In some examples, insertion tool 400 and/or any component thereof is disposable. For example, insertion tool 400 may be used during a single lead insertion procedure (or during two lead insertion procedures for a bilateral cochlear implant patient) and then disposed of. In this manner, insertion tool 400 does not need to be sterilized after use. Alternatively, insertion tool 400 may be sterilized after use so that it may be used in one or more subsequent lead insertion procedures.

Figure 19A:
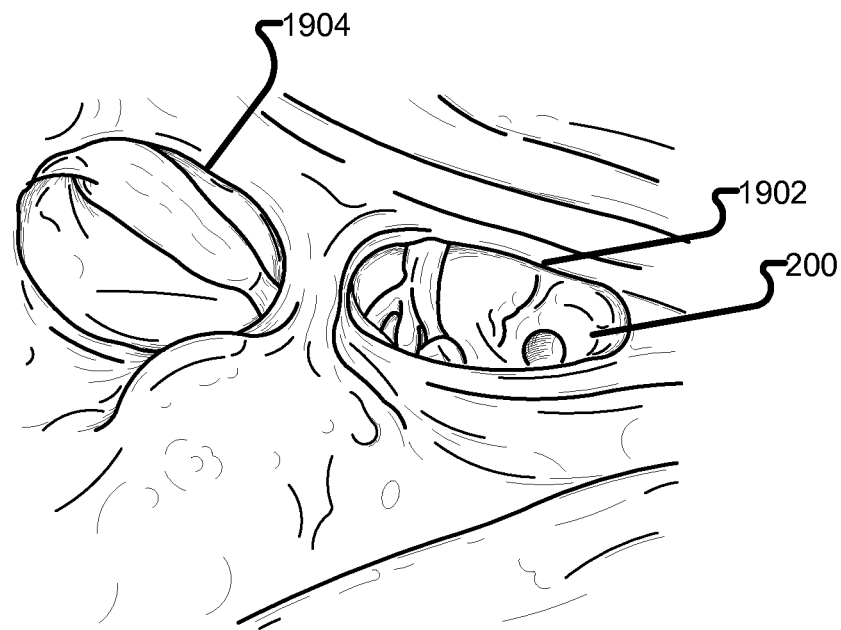
FIGS. 19A-19B show an exemplary facial recess that may be exposed within a cochlear implant patient during a lead insertion procedure according to principles described herein.
Figure 19B:
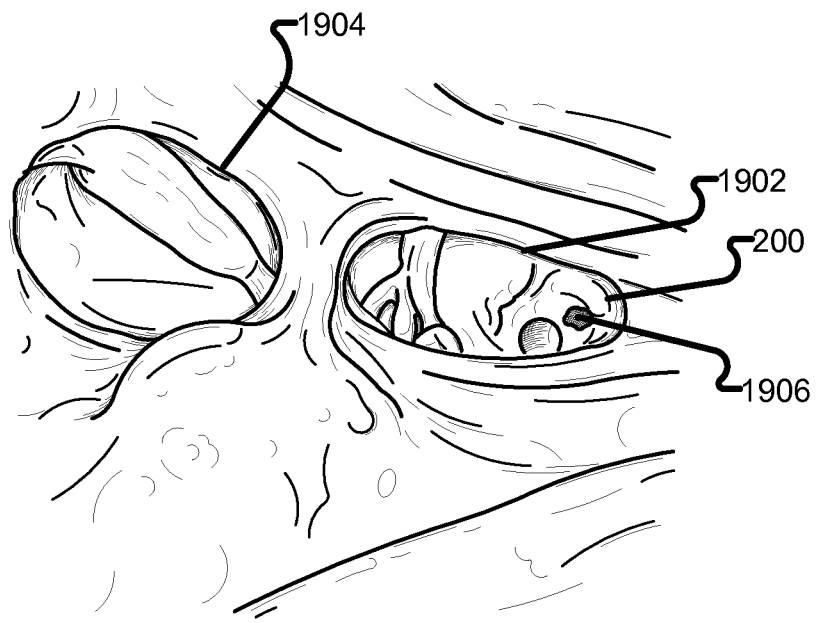

As mentioned, one of the advantages of insertion tool 400 is that insertion tool 400 may be used to insert lead 112 into a duct of the cochlea without insertion tool 400 being advanced into the facial recess. To illustrate, FIGS. 19A-19B show an exemplary facial recess 1902 that may be exposed within a cochlear implant patient during a lead insertion procedure. Facial recess 1902 includes the region bounded by the facial nerve and the chorda tympani and facilitates access to the cochlea 200. Round window 1904 is also shown in FIGS. 19A-19B. Round window 1904 may also facilitate access to one or more structures within the inner ear.

Once the facial recess 1902 has been exposed, a cochleostomy 1906 may be drilled into the cochlea 200. A lead 112 may then be inserted into the cochlea 200 by passing the lead 112 through the facial recess 1902 and cochleostomy 1906.

Figure 20:
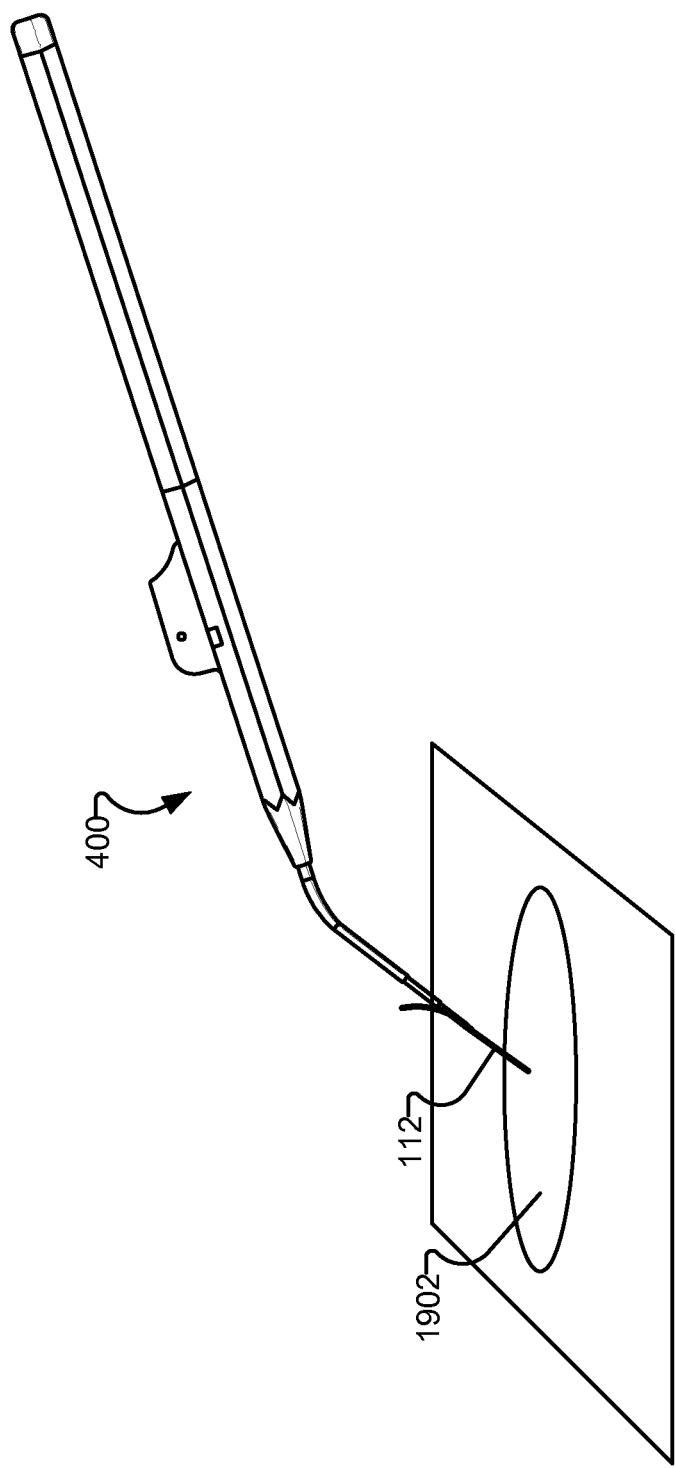
FIG. 20 illustrates an exemplary configuration wherein an insertion tool is used to insert a lead into the cochlea via a facial recess according to principles described herein.

FIG. 20 illustrates an exemplary configuration wherein insertion tool 400 is used to insert lead 112 into the cochlea via facial recess 1902. As shown in FIG. 20, insertion tool 400 may be configured to not enter the facial recess 1902 during the insertion procedure. In this manner, the risk of damaging the facial nerve, chorda tympani, or other internal structure with the insertion tool 400 is minimized or eliminated all together. Furthermore, jamming or other problems with the insertion tool 400 may be avoided by not allowing the insertion tool 400 to enter the facial recess 1902.

FIG. 20 also shows that the relatively thin profile of insertion tool 400 in combination with the angle of approach may provide an unobstructed view of the facial recess 1902 for the surgeon or other user of insertion tool 400. This may facilitate more accurate insertion of the lead 112 and minimize damage caused to various structures within the facial recess 1902.

As detailed above, the insertion tools, systems, and methods described herein may facilitate effective insertion of a lead into a cochlea or other bodily orifice. As an example, an exemplary insertion tool includes a handle assembly configured to facilitate handling of the insertion tool, an insertion assembly coupled to the handle assembly and comprising at least a rigid holding tube configured to removably couple to a proximal portion of the lead, and a release assembly disposed at least partially within the handle assembly and comprising at least a release button. The release assembly is configured to release the lead from the holding tube in response to user actuation of the release button.

An exemplary system configured to facilitate insertion of a lead into a bodily orifice includes a lead and an insertion tool. The lead includes a stimulation portion having a plurality of electrodes disposed thereon, a lead body configured to facilitate handling of the lead, and a jog portion configured to connect the lead body to the stimulation portion. The insertion tool includes a handle assembly, an insertion assembly coupled to the handle assembly and comprising at least a rigid holding tube having a receiving slot disposed therein that is configured to facilitate passage therethrough of the jog portion of the lead in order to facilitate removable coupling of the lead to the holding tube, and a release assembly disposed at least partially within the handle assembly and comprising at least a release button. The release assembly is configured to release the lead from the holding tube in response to user actuation of the release button.

An exemplary method of inserting a lead into a bodily orifice includes coupling a proximal portion of the lead to a holding tube that is a part of an insertion tool, guiding the lead into the bodily orifice with the insertion tool, and actuating a release button that is a part of the insertion tool. The actuating is configured to release the lead from the holding tube.

The preceding description has been presented only to illustrate and describe embodiments of the invention. It is not intended to be exhaustive or to limit the invention to any precise form disclosed. Many modifications and variations are possible in light of the above teaching.

What is claimed is:

1. An insertion tool configured to facilitate insertion of a lead having a plurality of electrodes disposed thereon at least partially into a bodily orifice, the insertion tool comprising:
    a handle assembly comprising
        a handle portion configured to facilitate handling of the insertion tool by a user and comprising a lumen extending at least partially therethrough, and
        a rigid handle tube coupled to a distal end of the handle portion and having a lumen extending therethrough, the lumen of the handle tube being in communication with the lumen of the handle portion;
    a release assembly disposed at least partially within the handle assembly and comprising a release button and a plunger disposed within a lumen of the handle portion and coupled to the release button; and
    an insertion assembly coupled to the handle assembly and comprising a rigid holding tube configured to removably couple to the lead and a flexible tube coupled to the proximal portion of the holding tube and to a distal portion of the plunger, the flexible tube configured to pass through the lumen of the handle tube;
    wherein the release assembly is configured to release the lead from the holding tube of the insertion assembly in response to a user actuation of the release button, the user actuation causing the plunger to retract within the lumen of the handle portion towards a proximal end of the handle portion, wherein the retraction of the plunger causes the flexible tube and the holding tube to retract away from the lead.

2. The insertion tool of claim 1, wherein:
    the handle tube comprises a curved portion such that a distal portion of the handle tube extends away from the handle portion at a predefined angle; and
    the handle tube is coupled to at least one component of the insertion assembly.

3. The insertion tool of claim 2, wherein the insertion assembly further comprises a rigid guide tube coupled to a proximal portion of the holding tube and to a distal portion of the handle tube, the guide tube configured to rotate to facilitate optimal orientation of the insertion assembly.

4. The insertion tool of claim 3, wherein:
    the guide tube comprises a slot partially extending along a length thereof; and
    the holding tube comprises an outwardly extending key member configured to fit within the slot of the guide tube;
    wherein the key member and slot are configured to facilitate longitudinal movement of the holding tube within the guide tube.

5. The insertion tool of claim 4, wherein the key member and slot are further configured to facilitate concurrent rotation of the guide tube and the holding tube.

6. The insertion tool of claim 3, wherein the guide tube comprises a sleeve configured to be coupled to the handle tube with an interference fit.

7. The insertion tool of claim 1, wherein the release assembly further comprises:
    a backstop member configured to be at least partially disposed within a lumen of the holding tube; and
    a wire affixed to the backstop member and configured to pass through a lumen of the flexible tube and the lumen of the handle portion, the wire being further affixed to a proximal portion of the handle portion;
    wherein the wire is configured to maintain the backstop member in a stationary position; and
    wherein the backstop member is configured to facilitate the release of the lead from the holding tube.

8. The insertion tool of claim 7, wherein the wire comprises Nitinol.

9. The insertion tool of claim 1, wherein the flexible tube comprises polytetrafluoroethylene.

10. The insertion tool of claim 1, wherein the plunger is coupled to a spring and configured to assume a non-retracted state upon user release of the release button.

11. The insertion tool of claim 1, wherein the release assembly further comprises a leaf spring configured to release the plunger in response to the user actuation of the release button.

12. The insertion tool of claim 1, wherein the user actuation of the release button comprises an advancing of the release button in a direction substantially parallel to a longitudinal axis of the handle portion.

13. The insertion tool of claim 1, wherein the holding tube comprises a receiving slot configured to facilitate the removable coupling of the holding tube to the lead.

14. A system comprising:
a lead comprising a stimulation portion having a plurality of electrodes disposed thereon, a lead body configured to facilitate handling of the lead, and a jog portion configured to connect the lead body to the stimulation portion; and
an insertion tool comprising
a handle assembly comprising
a handle portion configured to facilitate handling of the insertion tool by a user and comprising a lumen extending at least partially therethrough, and
a rigid handle tube coupled to a distal end of the handle portion and having a lumen extending therethrough, the lumen of the handle tube being in communication with the lumen of the handle portion;
a release assembly disposed at least partially within the handle assembly and comprising a release button and a plunger disposed within the lumen of the handle portion and coupled to the release button;
an insertion assembly coupled to the handle assembly and comprising
a rigid holding tube having a receiving slot disposed therein configured to facilitate passage therethrough of the jog portion of the lead in order to facilitate removable coupling of the jog portion to the holding tube, and
a flexible tube coupled to the proximal portion of the holding tube and to a distal portion of the plunger, the flexible tube configured to pass through the lumen of the handle tube; and
wherein the release assembly is configured to release the lead from the holding tube of the insertion assembly in response to a user actuation of the release button, the user actuation causing the plunger to retract within the lumen of the handle portion towards a proximal end of the handle portion, wherein the retraction of the plunger causes the flexible tube and the holding tube to retract away from the lead.

15. The system of claim 14, wherein:
the handle tube comprises a curved portion such that a distal portion of the handle tube extends away from the handle portion at a predefined angle; and
the handle tube is coupled to at least one component of the insertion assembly.

16. The system of claim 14, wherein the release assembly further comprises:
a backstop member configured to be at least partially disposed within a lumen of the holding tube; and
a wire affixed to the backstop member and configured to pass through a lumen of the flexible tube and the lumen of the handle portion, the wire being further affixed to a proximal portion of the handle portion;
wherein the wire is configured to maintain the backstop member in a stationary position; and
wherein the backstop member is configured to facilitate the release of the lead from the holding tube.

17. The system of claim 14, wherein the user actuation of the release button comprises an advancing of the release button in a direction substantially parallel to a longitudinal axis of the handle portion.

18. The system of claim 17, wherein the advancing of the release button is in a distal direction.

19. A method of inserting a lead into a bodily orifice, the method comprising:
coupling a portion of the lead to a holding tube that is a part of an insertion tool, the insertion tool comprising:
a handle assembly comprising
a handle portion configured to facilitate handling of the insertion tool by a user and comprising a lumen extending at least partially therethrough, and
a rigid handle tube coupled to a distal end of the handle portion and having a lumen extending therethrough, the lumen of the handle tube being in communication with the lumen of the handle portion;
a release assembly disposed at least partially within the handle assembly and comprising a release button and a plunger disposed within a lumen of the handle portion and coupled to the release button; and
an insertion assembly coupled to the handle assembly and comprising the holding tube configured to removably couple to the lead and a flexible tube coupled to the proximal portion of the holding tube and to a distal portion of the plunger, the flexible tube configured to pass through the lumen of the handle tube;
guiding the lead at least partially into the bodily orifice with the insertion tool; and
actuating the release button to release the lead from the holding tube, wherein the actuating causes the plunger to retract within the lumen of the handle portion towards a proximal end of the handle portion, and wherein the retraction of the plunger causes the flexible tube and the holding tube to retract away from the lead.

20. The method of claim 19, wherein the guiding of the lead comprises inserting the lead through a facial recess without allowing the insertion tool to enter the facial recess.

* * * * *